United States Patent
Li et al.

(10) Patent No.: US 9,568,423 B2
(45) Date of Patent: Feb. 14, 2017

(54) SYSTEM AND METHOD FOR DETECTING MULTIPLE-EXCITATION-INDUCED LIGHT IN A FLOW CHANNEL

(71) Applicant: ACEA BIOSCIENCES, INC, San Diego, CA (US)

(72) Inventors: Nan Li, San Diego, CA (US); Jian Wu, Hangzhou (CN); Ye Chen, Hangzhou (CN); Tianxing Wang, Hangzhou (CN); Xiaobo Wang, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 106 days.

(21) Appl. No.: 13/657,845

(22) Filed: Oct. 22, 2012

(65) Prior Publication Data
US 2013/0200277 A1    Aug. 8, 2013

Related U.S. Application Data

(60) Provisional application No. 61/550,243, filed on Oct. 21, 2011.

(51) Int. Cl.
*G01N 21/64*    (2006.01)
*G01F 1/00*    (2006.01)
(Continued)

(52) U.S. Cl.
CPC .......... *G01N 21/64* (2013.01); *G01N 15/1429* (2013.01); *G01N 15/1434* (2013.01);
(Continued)

(58) Field of Classification Search
CPC ................................................. G01N 15/1438
(Continued)

(56) References Cited

U.S. PATENT DOCUMENTS

| 4,482,994 A | 11/1984 | Ishikawa |
| 4,573,796 A * | 3/1986 | Martin et al. ................. 356/318 |

(Continued)

FOREIGN PATENT DOCUMENTS

| WO | 03/021241 A1 | 3/2003 |
| WO | 2011003073 A1 | 1/2011 |

OTHER PUBLICATIONS

EP12841762.3 Extended European Search Report mailed Mar. 27, 2015.
EP12845835, European Search Report mailed Jul. 1, 2015.

*Primary Examiner* — David Porta
*Assistant Examiner* — Carolyn Igyarto
(74) *Attorney, Agent, or Firm* — Wagenknecht IP Law Group PC

(57) ABSTRACT

A system for detecting signal components of light induced by multiple excitation sources including: a flow channel including at least two spatially separated optical interrogation zones; a non-modulating excitation source that directs a light beam of a first wavelength at a near constant intensity onto a first of the optical interrogation zones; a modulating excitation source that directs a light beam of a second wavelength with an intensity modulated over time at a modulating frequency onto a second of the optical interrogation zones; a detector subsystem comprising a set of detectors configured to detect light emitted from particles flowing through the at least two optical interrogation zones and to convert the detected light into a total electrical signal; and a processor that determines signal components from the light detected from each of the optical interrogation zones.

14 Claims, 19 Drawing Sheets

(51) Int. Cl.
*G01N 15/14* (2006.01)
*G01N 15/10* (2006.01)

(52) U.S. Cl.
CPC ....... *G01N 15/1459* (2013.01); *G01N 21/645* (2013.01); *G01N 21/6428* (2013.01); *G01N 2015/1006* (2013.01); *G01N 2015/149* (2013.01); *G01N 2015/1438* (2013.01); *G01N 2021/6419* (2013.01); *G01N 2021/6421* (2013.01); *G01N 2021/6441* (2013.01); *G01N 2021/6482* (2013.01)

(58) Field of Classification Search
USPC .......................... 250/356.1, 367, 393, 459.1
See application file for complete search history.

(56) References Cited

U.S. PATENT DOCUMENTS

| | | | |
|---|---|---|---|
| 4,707,064 A | 11/1987 | Dobrowolski et al. | |
| 5,674,698 A | 10/1997 | Zarling et al. | |
| 5,760,900 A | 6/1998 | Ito et al. | |
| 5,865,520 A | 2/1999 | Kavanagh et al. | |
| 5,930,048 A | 7/1999 | Kaneko | |
| 6,558,945 B1 | 5/2003 | Kao | |
| 2007/0096039 A1 | 5/2007 | Kapoor et al. | |
| 2008/0055595 A1 | 3/2008 | Olson et al. | |
| 2008/0213915 A1 | 9/2008 | Durack et al. | |
| 2008/0283754 A1* | 11/2008 | Nerin et al. | 250/339.05 |
| 2009/0141327 A1 | 6/2009 | Penn et al. | |
| 2009/0296242 A1 | 12/2009 | Callen et al. | |
| 2009/0297490 A1 | 12/2009 | Nakamura et al. | |
| 2010/0108910 A1 | 5/2010 | Morrell et al. | |

* cited by examiner

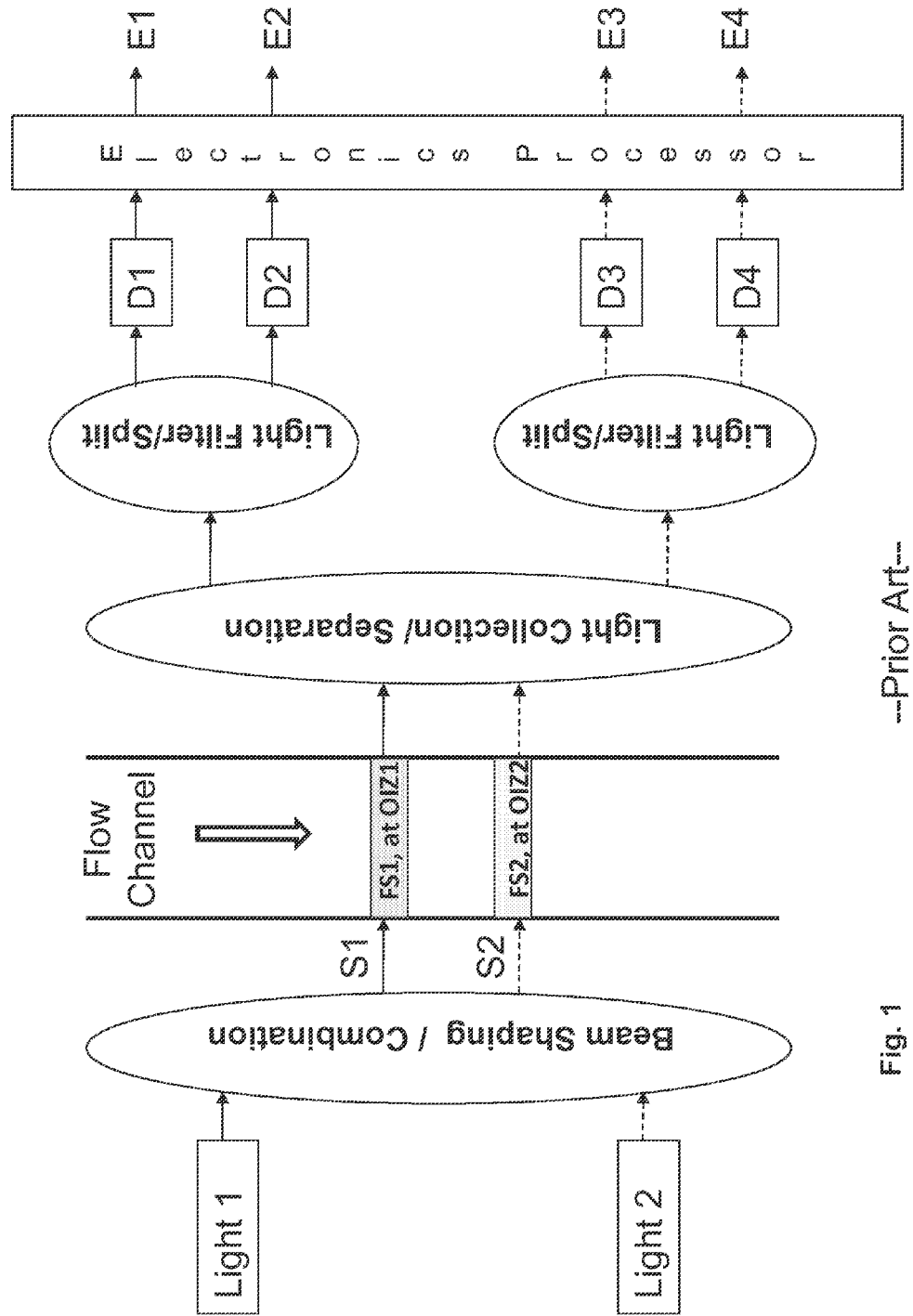
Fig. 1 —Prior Art—

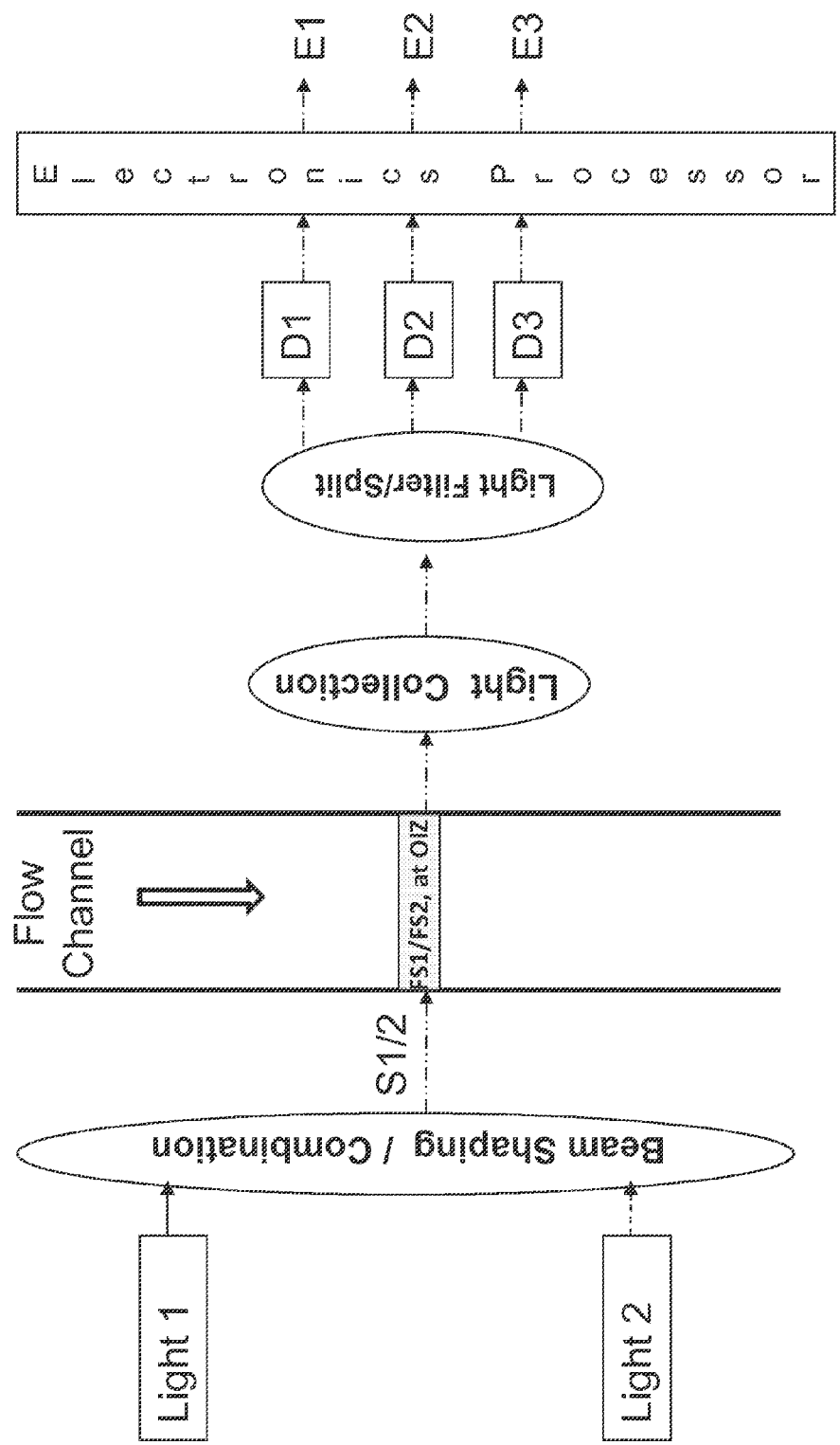
Fig. 2 --Prior Art--

SYSTEM AND METHOD FOR DETECTING MULTIPLE-EXCITATION-INDUCED LIGHT IN A FLOW CHANNEL

CROSS REFERENCE TO RELATED APPLICATIONS

This application claims benefit of priority to U.S. provisional patent application Ser. No. 61/550,243, filed Oct. 21, 2011; the contents of which are herein incorporated by reference in their entirety.

TECHNICAL FIELD

This invention relates generally to the field of detecting light emitted from fluorescent molecules excited by multiple excitation light sources, and more specifically to a system and method that incorporates at least one intensity modulated excitation light source and a nonmodulated light source to induce the emission of light from at least two spatially separated optical interrogation zones of a flow channel and the detection and measurement thereof.

BACKGROUND OF THE INVENTION

Flow cytometer is an instrument for measuring/analyzing individual fluorescently-labeled particles/cells being lined up and flown through a flow channel under hydrodynamic focusing or other focusing forces. Light beam from individual light sources (e.g. laser) of particular wavelengths is shaped typically to an elliptical or rectangular shape with the major/long axis (about 50 to 200 microns) perpendicular to the flowing direction of the particles/cells in a flow channel and minor/short axis (about 10 to 30 microns) parallel to the flowing direction of the particles/cells and is guided/directed to optical interrogation zones (OIZ) in the flow channel. As the fluorescently-labeled particles/cells pass through the light beam one-by-one in the optical interrogation zones, multiple physical characteristics of single cells can be detected and measured. The properties measured include a particle's relative size (Forward Scatter, i.e. FSC), relative granularity or internal complexity (Side Scatter, i.e. SSC), and relative fluorescence intensity (i.e., fluorescence signals from fluorescent molecules in the labeled cells under excitation by light sources.). These characteristics are determined using an optical-to-electronic coupling system (i.e. photodetector) that records how the cell or particle scatters incident laser light and emits fluorescence.

Traditionally, two approaches have been implemented for flow cytometers with multiple-excitation light sources. In the first approach, the shaped elliptical laser beams from multiple sources (e.g., S1, S2 in FIG. 1) of different wavelengths propagate across the flow channel and form two optical interrogation zones (OIZ) at different vertical locations along the flow channel, spaced at certain distance in the range of, e.g., 100 to 200 microns. Thus when a cell flows through the flow channel, it will pass the individual OIZ (e.g. OIZ1 corresponding to laser beam S1 and OIZ2 corresponding to laser beam S2 in FIG. 1) in sequence. Consequently, light in the laser beams will be scattered and fluorescent light will be emitted as well by different fluorescent molecules (FM) possessed by the cell. Multiple fluorescent signals (FS) with different peak wavelengths may be emitted by different molecules at one OIZ. For example, S1 can be 488 nm laser and S2 can be 640 nm laser. Fluorescent molecules FITC, PE, and PE-Cy7 can be excited by S1 (488 nm) and emit light at peak wavelength of 519 nm, 578 nm, and 785 nm respectively whilst APC and APC-Cy7 can be excited by S2 (640 nm) and emit light at peak wavelength of 660 nm and 785 nm respectively. It is possible that the spectra of the fluorescent signals excited by different light sources are overlapped (e.g. PE-Cy7 and APC-Cy7 are both emitted at a peak wavelength of 785 nm, but need to be excited by different wavelengths). Therefore, it would be essential that the fluorescent signals excited by different light sources (e.g. FS1 being excited by S1 and FS2 being excited by S2 in FIG. 1) are separated by the light collection and separation optics for effective detection of these fluorescent signals. Otherwise, the flexibility of choosing the fluorochrome for cell staining would be limited and it becomes a shortcoming for a flow cytometer. Through light collection/separation optics, the fluorescent signal FS1 and FS2 is collected and separated to different physical positions with a spatial distance large enough to accommodate the filters and photodetectors for light splitting, filtering, and detection. This light splitting, filtering, and detection system resolves the quantities of each corresponding fluorescent molecule, thus are referred to fluorescence (FL) channels in flow cytometry. For example, fluorescent signal FS1 emitted from OIZ1 is then further split and detected by photodetector D1 and D2 at two different emission wavelengths to resolve the quantity of fluorescent molecule FM1 (e.g., FITC) and FM2 (e.g., PE-Cy7) respectively and fluorescent signal FS2 emitted from OIZ2 is then further split and detected by photodetector D3 and D4 at two different emission wavelengths to resolve the quantity of fluorescent molecule FM3 (e.g., APC) and FM4 (e.g., APC-Cy7). Photodetectors convert the detected fluorescent signals into electronic signals. Using electronic processors, such electronic signals are then filtered, amplified and converted into digital signals, and further processed to derive various characteristics of each corresponding fluorescent molecule. For example, output E1 and E2 correspond to the signals of FM1 and FM2 respectively and output E3 and E4 correspond to the signals of FM3 and FM4 respectively. When a particle/cell passes through an OIZ, an electronic pulse will be generated at the corresponding detection channel and such cell/particle induced electronic pulse is characterized by its height, area, and width to reveal the property of the particles/cells. For example, the height of the pulse detected by one FL channel provides a good indication of the intensity of the corresponding fluorescent molecule. In summary, in a flow cytometer with a system configured shown in FIG. 1 and as described above, fluorescent signals excited by different light sources is physically/optically separated for detection with different photodetectors, and fluorescent molecules with overlapped emission spectra could be used to label the particles/cells in the same experiment.

However, the first approach has several limitations. (1) Complex optics system are needed to collect and to separate light from different OIZs in order to achieve an efficient and clear separation of light emitted from each OIZ with small physical separation distances of about 100-200 microns. (2) Accurate control and delivery of excitation beams to the flow channel is required to have an accurate control of separation distance between OIZs. In a flow cytometer, an individual cell is usually transported through the flow channel at a constant speed, which means that the time interval between the detected digital pulse generated in OIZ1 and the detected digital pulse generated in OIZ2 will be fixed. Therefore, in order to correlate signals from the same cell passing through different OIZs, this time interval should be controlled accurately as well. Furthermore, light emitted from each OIZ is separated out from each other using a collection and separation optics system and detected by a different set of filters and photodetectors. The efficiency of light collected and delivered to photodetectors for each OIZ depends on the separation distances between OIZs. If the separation distance between these OIZs varies due to any factors such as temperature, pressure, misalignment during instrument shipping, or other system instability factors, it may affect not only the time interval between detected pulses generated in two OIZs but also, more importantly, the efficiency of light collection for each OIZ, leading to unreliable measurement results of the signals. (3) The optical setup is not efficient because each photodetector is used to detect only one type of fluorescent molecule (i.e. having a pre-determined excitation wavelength and emission bandwidth). For example, in a system as illustrated in FIG. 1, four detection channels (E1 to E4) are needed to record the signals from four fluorescent molecules (FM1 to FM4). If FM2 (e.g. PE-Cy7) and FM4 (e.g. APC-Cy7) are assumed to have the same/overlapped emission spectrum but need to be excited by S1 and S2 respectively, two sets of band-pass filters and photodetectors are still needed for effective detection. Combining of the detection of FM2 and FM4 with one band-pass filter and one photodetector is not possible in this configuration. This results in the increased complexity and therefore increased cost of the whole system.

In the second approach, the shaped, elliptical laser beams from multiple sources (e.g., S1, S2 in FIG. 2) of different wavelengths propagate across the flow channel at a single vertical location along the flow channel, forming a single optical interrogation zone (OIZ). Thus when a particle/cell flows through the flow channel, it will pass the OIZ and will be subjected to multiple laser beams simultaneously. Consequently, light in laser beams will be scattered and fluorescent light will be emitted by fluorescent molecules (FM) possessed by the cell. Multiple fluorescent signals with same/overlapped or different emission peak wavelengths may be emitted by different fluorescent molecules excited by multiple laser beams at the OIZ. For example, S1 and S2 can be 488 nm and 640 nm laser, respectively. Fluorescent molecules FITC and PE-Cy7 can be excited by S1 (488 nm) and emit light at peak wavelength of 519 nm and 785 nm, respectively, whilst fluorescent molecules APC and APC-Cy7 can be excited by S2 (640 nm) and emit light at peak wavelength of 660 nm and 785 respectively. Through light collection optics, the fluorescent signals emitted from the particle/cell in the OIZ would be collected, and then further split or filtered into different wavelength ranges and is detected by photodetectors, converting optical signals into electronic signals. For example, fluorescent signals emitted from OIZ is split and detected by D1, D2 and D3 at three different emission wavelengths to resolve quantity of fluorescent molecules FM1 (e.g., FITC) and FM2 (e.g., PE-Cy7 or PE-Cy7) and FM3 (APC). Using electronic processors, electronic signals are then filtered, amplified and converted to digital signals, and further processed to derive various characteristics of each corresponding fluorescent molecule. For example, output E1, E2 and E3 correspond to the signals of FM1, FM2 and FM3, respectively. This second approach, as schematically represented in FIG. 2, has some advantages. There is no need for complex optical system for separating fluorescent signals excited by multiple light sources. Furthermore, the optical setup in this approach is efficient since the same set of optical filter and photodetector could be used for detection of fluorescent molecules having the same emission peak wavelengths but different excitation wavelengths. For example, whilst PE-Cy7 and APC-Cy7 are excited by 488 nm and 640 nm respectively, both molecules can be detected using the same set of band-pass filter and one photodetector for monitoring wavelength ranges centered at 785 nm, as long as these two dyes are not used in the same experiment. On the other hand, this approach has a major limitation that it could not distinguish the fluorescent signals from different fluorescent molecules having the same emission spectra even if they are excited by different lasers. For example, the system of such a configuration as schematically shown in FIG. 2 could not be used to distinguish and reliably detect fluorescent signals from molecules of PE-Cy7 (excited by 488 nm laser) and APC-Cy7 (excited by 640 nm laser) in the same experiment, even though they have different excitation wavelengths.

A relatively recent method, published in U.S. Pat. No. 7,990,525, describes an extension of this second approach where the excitation laser light is time-multiplexed so that each light source is switched on and off at a very fast rate. At any time moment, no two (or more) light sources are switched on simultaneously. Thus, either no light source or only one light source is switched on by appropriate control of light sources. The detection electronics can be used in synchronization so that the fluorescence signals excited by different lasers could be isolated, recovered, and analyzed. It is required that the multiple excitation light beams are directed/focused to the same OIZ, and consequently there is no time interval between detected electronic signals excited by different excitation light sources as seen for the first approach. However, this approach possessed other limitations. Firstly, in order to eliminate the above-mentioned time interval issue, it requires precise combination and alignment of the light beams from different excitation light sources to be coaxial and overlapped at the same location across the flow channel. Secondly, for reliable recovery and isolation of the emitted fluorescent signals excited by different excitation light sources as a particle/cell passes through the OIZ, accurate control of the time-multiplexed illumination of multiple excitation light beams is essential as well as the subsequent synchronization of the signal processing electronics. Thirdly, the time-multiplexed illumination of multiple excitation light sources corresponds to a fact that the time interval for a cell/particle to pass through the OIZ is shared between multiple excitations. Consequently, a single particle-induced electronic pulse generated when the particle/cell passes through the OIZ is time-shared between multiple excitations as well. If the same amount of data points is needed to effectively recover such particle-induced electronic pulse information for each of the multiple excitations, a faster multiplexing illumination rate and a faster sampling frequency for the signal processing electronics is required. Furthermore, such issue would become more severe especially when the number of the excitation light sources increases. Fourthly, such configuration requires that one excitation light source is OFF when another one is ON. However, due to stray current of the electronic signal for the digital modulation of the laser source and/or the property of the laser source (i.e. modulation ratio is not high enough so that there is still low level of light from the light source even when it is controlled to be OFF), such OFF-status light source will still contribute some illumination to the OIZ thus increase the background for detection and measurement of the emitted fluorescent signal excited by another ON-status light source, affecting the system sensitivity for detecting low-level, dim fluorescent particles/cells.

Another recent method, published in U.S. Pat. No. 8,077,310, also describes a further extension of the previously described second approach where two excitation sources emit lights at different wavelengths onto a single location on a flow channel. The multiple excitation sources are controlled to operate between such operation modes: a first mode wherein only one of multiple excitation sources emits light onto the single location and a second mode wherein both excitation sources emit lights onto the single location. The approach further comprises a detector subsystem that detects lights emitted from the single location and generates a composite signal and a processor to separate the composite signal into component signals due to each of two excitation sources. Since the multiple excitation light beams are directed to the same single location on the flow channel, consequently there is no time interval between detected electronic signals excited by different excitation sources as seen for the first approach. By switching between different operation modes, composite signals corresponding to these operation modes are generated and can be processed to result in isolated signals due to each individual excitation sources. This approach provides a possibility of, in a single experiment, using different fluorescent molecules having the same emission spectra but with different excitation wavelengths. However, such an approach has limitations due to emitting multiple excitation sources onto a single location on the flow cell and simultaneous turn-on of multiple excitation sources at some time moments.

Still other approaches have been suggested or described in recent years, relating to emitting multiple excitation light sources onto a flow channel and detecting and separating emission fluorescent lights due to these excitation sources. For example, US 2008/0213915 described an approach where multiple excitation light sources are all modulated with each source being modulated at different frequencies. The modulated excitation beams are combined and guided onto single or multiple focused spots or locations on the flow channel. The fluorescent emissions from particles due to modulated excitation beams are detected to produce detector output signals, which are then processed to distinguish the fluorescent signals caused by each individual excitation beam. In another example, US 2007/0096039 described an approach for analyzing objects having multiple fluorescing species in a fluid stream. Multiple intensity-modulated excitation light beams, each of which is modulated at a unique frequency between 2 and 100 MHz, are combined and directed to one or more interrogation zones on a flow cell and will interact with the passing objects in a fluid stream in the flow cell. The fluorescence emission light from fluorescent species in the objects is detected with one or more photosensitive detectors and resulted electronic signals are analyzed to extract multiple component emission signals, each of which corresponds to one excitation light beam. These approaches have limitations associated with the requirement of modulation of all excitation sources at unique frequencies and the ineffectiveness in the de-modulation methods in achieving high signal-noise ratios. Thus, there remains a need to develop a novel approach for effective detection of emission light by multiple excitation light sources from a flow channel.

SUMMARY OF THE INVENTION

In one aspect of the invention, a system for detecting signal components of light induced by multiple excitation sources is provided, which includes: a flow channel configured for the flow of particles, the flow channel including at least two spatially separated optical interrogation zones; a non-modulating excitation source that directs a light beam of a first wavelength at a near constant intensity onto a first of the optical interrogation zones; a modulating excitation source that directs a light beam of a second wavelength with an intensity modulated over time at a modulating frequency onto a second of the optical interrogation zones, wherein the second wavelength is different from the first wavelength; a detector subsystem comprising a set of detectors configured to detect light emitted from particles flowing through the at least two optical interrogation zones and to convert the detected light into a total electrical signal; and a processor configured to receive the total electrical signal from the detector subsystem, to de-modulate electrical signal that is modulated, and to determine signal components from the light detected from each of the optical interrogation zones.

In some embodiments, the system further includes a third optical interrogation zone spatially separated from the first and second optical interrogation zones; and another excitation source that directs a light beam onto the third optical interrogation zone. In one example of such embodiment, the excitation source that directs the light beam onto the third optical interrogation zone is a second non-modulating excitation source that directs the light beam of a third wavelength at a near constant intensity onto the third optical interrogation zone, wherein the third wavelength is different from both the first wavelength and the second wavelength. In another example of such an embodiment, the excitation source that directs the light beam onto the third optical interrogation zone is a second modulating excitation source that directs the light beam of a third wavelength with an intensity modulated over time at a modulating frequency.

In another aspect of the present invention, a method of detecting signal components from light induced by multiple excitation sources is provided, the method including: providing a flow channel including at least two spatially separated optical interrogation zones; flowing a population of particles labeled with at least two different fluorescent molecules through each of the optical interrogation zones; directing a light beam of a first wavelength at a near constant intensity onto a first of the optical interrogation zones to induce emission of light from the fluorescence-molecule containing particles; directing a light beam of a first wavelength with an intensity modulated over time according to a modulating frequency onto a second of the optical interrogation zones to induce emission of light from the fluorescence-molecule containing particles, wherein the second wavelength is different from the first wavelength; detecting the light emitted from the particles from each of the optical interrogation zone and converting detected light into a total electrical signal; de-modulating electrical signal from the total electrical; and determining signal components of the light detected from each of the optical interrogation zones.

In some embodiments the method includes flowing the population of particles through a third optical interrogation zone spatially separated from the first and second optical interrogation zones; directing a light beam of a third wavelength at a near constant intensity onto the third optical interrogation zone to induce emission of light from the fluorescence-molecule containing particles, wherein the third wavelength is different from the first and second wavelengths; detecting the light emitted from the particles flowing through the third optical interrogation zone and converting the detected light into the total electrical signal.

In a related embodiment, the method includes flowing the population of particles through a third optical interrogation zone spatially separated from the first and second optical interrogation zones; directing a light beam of a third wavelength with an intensity being modulated over time at the modulating frequency onto the third optical interrogation zone to induce emission of light from the fluorescence-molecule containing particles, wherein the third wavelength is different the first and second wavelengths; and detecting the light emitted from the particles flowing through the third optical interrogation zone and converting the detected light into the total electrical signal.

For the present invention, multiple excitation light sources can comprise at least 2 light sources of different wavelengths. In one embodiment of the invention, the multiple light sources comprise 2 light sources having different wavelengths. During operation, one light source is not intensity modulated and one light source is intensity-modulated. In another embodiment of the invention, the multiple light sources comprise 3 light sources having different wavelengths. During operation, at least one light source is not modulated and at least one light source is intensity-modulated. For example, in one embodiment, one light source is intensity-modulated and the other two light sources are not modulated. For such an embodiment, the light beams from the three light sources may be arranged along the flow cell in such an order that the modulated light beam is positioned in the middle with the two un-modulated light beams positioned each at one side (or end) of the modulated beam along the flow cell. In another embodiment, one light source is not modulated and the other two light sources are intensity-modulated. For such an embodiment, the light beams from the three light sources may be arranged along the flow cell in such an order that the un-modulated light beam is positioned in the middle with the two modulated light beams positioned each at one side (or end) of the un-modulated beam along the flow cell. The modulation frequencies of two intensity-modulated light sources may be different. In certain preferred embodiment, the modulation frequencies of two intensity-modulated light sources are the same. In still another embodiment of the invention, the multiple light sources comprise 4 light sources having different wavelengths. During operation, at least one light source is not modulated and at least one light source is intensity-modulated. For example, in one embodiment, two light sources are intensity-modulated and the other two light sources are not modulated. For such an embodiment, the light beams from the four light sources may be arranged along the flow cell in such an order that the un-modulated light beam and modulated light team are positioned in an alternative manner. The modulation frequencies of two intensity-modulated light sources may be different. In certain preferred embodiment, the modulation frequencies of two intensity-modulated light sources are the same. In still another embodiment of the invention, the multiple light sources comprise more than 4 light sources having different wavelengths. A light source could be a laser, a laser emitting diode (LED) or other light generating component. At least one of the multiple light sources can be modulated and at least one of the multiple light sources is not modulated and thus maintains a constant or near constant intensity. For N light sources (N is the total number of different excitation light sources with different wavelength), some light sources can be modulated and other light sources are not-modulated. Preferably, light beams from these light sources may be arranged along the flow cell in such an order that the un-modulated light beam and modulated light team are positioned in an alternative manner. The modulation frequencies of those intensity-modulated light sources may be different. In certain preferred embodiments, the modulation frequencies of the intensity-modulated light sources are the same. Light sources can be either analogue modulated or digitally modulated. In analogue modulation, light intensity from the light source can be controlled to be proportional to the amplitude of the analogue signals used for analogue modulation. The analogue signals used for modulation can be of different waveforms, including sine-waveform, triangular-waveform, and seesaw-waveform. In digital modulation, light from the light source can be turned on and off by the digital signals used for digital modulation. The light source can be modulated at any suitable frequencies, as long as the modulated particle-induced (or cell-induced) electronic pulses can be de-modulated through electronics-processing means to recover the particle-induced electronic pulse.

Each optical interrogation zone corresponds to a region where the light beam from an excitation light source is propagating across the flow channel. The light beam typically has an "elliptical" or "rectangular" shape with the major/long axis perpendicular to the flowing direction of the particles/cells in a flow channel and minor/short axis parallel to the flowing direction of the particles/cells in a flow channel. In one embodiment, the minor/short axis of the light beams is between about 5 and 30 microns and the major/long axis of the light beam is between 50 and 200 microns. Preferably, the minor/short axis of the beam is between 10 and 20 microns. Preferably, the major/long axis of the beam is between 60 and 100 microns. The light illumination sub-system of the present invention shall include beam-shaping optical components to shape the beam to the desired shape and power distribution.

In the present invention, the optical interrogation zones may be separated from each other and arranged to be at different locations along the flow channel such that a cell or particle flows through a series of optical interrogation zones with the center-to-center distance between adjacent optical interrogation zones of different values. In one embodiment, the excitation beam has a elliptical shape whose minor axis is 10 microns. The center-to-center distance between adjacent OIZs could be as large as more than 500 microns. Preferably, the center-to-center distance between adjacent OIZs is between 10 microns and 300 microns. Even more preferably, the center-to-center distance between adjacent OIZs is between 20 microns and 200 microns. Still more preferably, the center-to-center distance between adjacent OIZs is between 25 microns and 100 microns. Still more preferably, the center-to-center distance between adjacent optical interrogation zones is between 30 microns and 80 microns. Still more preferably, the center-to-center distance between adjacent optical interrogation zones is between 35 microns and 70 microns. The choice of the center-to-center distance between adjacent OIZs should be dependent on a number of factors, including the minor axis of light beam along the flow direction at OIZs, the light collection efficiency for light emitted from different OIZs, the flow speed range of particles/cells flowing inside the flow channel and the particle/cell concentration range. Preferably, the light beams at adjacent OIZs do not overlap. For example, if the excitation beam has an elliptical shape whose minor axis is 15 microns parallel to the flow direction, the center-to-center distance between adjacent OIZs is preferably between 15 microns and 150 microns, leaving the gap between the adjacent light beams propagating through the flow channel in the range of 0 to 135 microns. In one embodiment, if the center-to-center distance is 30 microns for the beams with 15 micron in minor axis beams, the gap between the adjacent light beams is 15 microns. The light illumination sub-system of the present invention shall include beam-steering and/or beam combining and/or light focusing and/or other optical components to deliver excitation light beams with required beam shape to different locations with required center-to-center distance along the flow channel.

A detection sub-system includes light collection optics capable of collecting light emitted from different optical interrogation zones. The collected light is then split or filtered into light of interest with different wavelength ranges and is detected via photodetectors such as PMT (photomultiplier tubes), APD (avalanche photodiodes) and the like. In the present invention, the emitted light from all the OIZs is collected and then preferably filtered by band-pass filters to split all the collected light into different wavelength ranges. Then a set of corresponding photodetectors convert the light signals into electronic signals and such electronic signals are processed by an electronics processor using methods including amplification, multiplying with a signal, filtering, de-modulation, A/D conversion, signal recovery means, etc. Since at least one excitation light source in the present invention may be modulated, the resulting electronics signal, i.e. particle-induced (or cell-induced) pulse from the photodetector would be correspondingly modulated as well. De-modulation and signal-recovery-means are used to recover these particle-induced pulses and correlate each individual particle-induced pulse to its excitation wavelength. Different de-modulation and signal-recovery-means can be employed, including single-side demodulation, quadrature demodulation and square-wave demodulation. In this way, the filter and photodetector set for detecting the same emission wavelength range can be shared even though the emission light may be excited by different excitation light sources. Therefore, it shows advantages over the first approach in the prior art, as schematically represented in FIG. 1. In addition, there is no strict requirement for the location of optical interrogation zones for effective detection using present invention, as long as the separation distance of the adjacent OIZs are properly selected so that the probability of two particles/cells being both within two OIZs is minimized or very low. Therefore, the change of the separation distance of the OIZs caused by any factors such as temperature, pressure, misalignment during instrument shipping, or other system instability factors, will not affect the measurement results of the signals. Furthermore, as an advantage over the time-multiplexed illumination of multiple excitation light beams in U.S. Pat. No. 7,990,525, the system and method in the present invention do not need for accurate synchronization between the modulations of each excitation light source (i.e., the modulation of each excitation light source is independent of each other).

In addition, compared with the approaches described in U.S. Pat. No. 8,077,310 where light from different excitation sources emit to the same location on the flow cell, the system and method in the present invention directs light from different excitation sources onto different locations, allowing for the use of full dynamic range of photodetectors for detecting the fluorescent signals caused by each individual light excitation source and minimizing possible interference or crosstalk between fluorescent signals caused by different excitation sources.

Finally, compared with approaches described in US 2007/0096039 and US 2008/0213915 where multiple excitation light sources are all modulated with each source being modulated at different frequencies, the system and method in the present invention require that at least one light source is not modulated. In addition, when multiple light sources are intensity-modulated, their modulation frequencies are preferably to be the same. These approaches offer significant advantages in reducing the complexity of electronic-processor sub-systems and in improving the system performance such as signal-to-noise ratio, signal process flow as well as data analysis and process speed.

BRIEF DESCRIPTION OF DRAWINGS

FIG. 1 is a schematic representation of a prior flow cytometry light illumination approach with two excitation light sources. Light beams are arranged or directed to two optical interrogation zones, separated at a fixed distance along the flow channel. Light emitted from different OIZs is collected and optically/physically separated. Separated light components due to different excitation sources are then split or filtered into light components of different wavelength ranges and are detected by photodetectors. The electronic signals from photodetectors are processed using electronics processor. Each electronic signal output corresponds to light emitted from one optical interrogation zone at a particular wavelength range due to one excitation source.

FIG. 2 is a schematic representation of a prior flow cytometry light illumination approach with two excitation light sources. Light beams from the two excitation light sources are directed to a single optical interrogation zone (OIZ). Light emitted from the OIZ is collected and then split or filtered into light components of different wavelength ranges and are detected by photodetectors. The electronic signals from photodetectors are processed using electronics processor. Electronic signal output corresponds to light emitted from the optical interrogation zone at a particular wavelength range due to either one of the light source or both.

FIG. 3A depicts a preferred embodiment, where one light source S2 is modulated and the other S1 is not modulated. FIG. 3B depicts a preferred embodiment, where two light sources S2 are modulated and another light source S1 is not modulated Using de-modulation and signal-recover means, electronics processor can de-modulate the electronic signals from the photodetectors to recover particle-induced electronic pulse due to either light source.

Figure 3A:
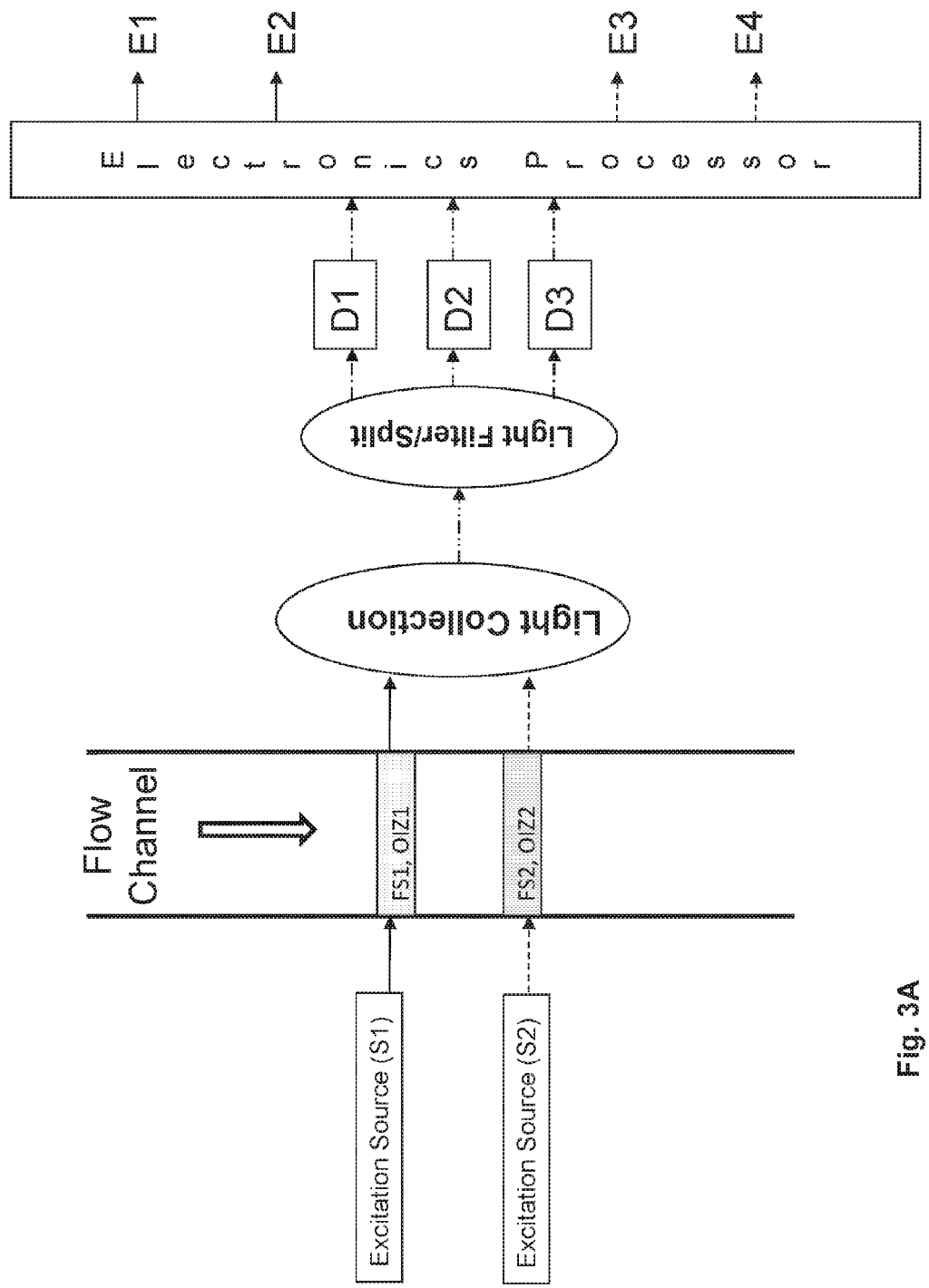
FIG. 3A shows an exemplary schematic representation of the present invention where a light illumination sub-system directs light beams from two excitation light sources S1, S2 to two optical interrogation zones OIZ1, OIZ2, separated at some distances along the flow channel.

the intermediate de-modulation signal used to recover the $2^{nd}$ particle-induced electronic pulse; 4G) recovered $1^{st}$ pulse profile; and 4H) recovered $2^{nd}$ pulse profile.

FIG. 5 shows the process of analogue modulation of light sources and de-modulation of electronic signals to recover particle-induced electronic pulse, as a particle/cell passes through two optical interrogation zones: 5A) an analogue signal used to modulate the $1^{st}$ light source (3 MHz); 5B) detected electronic signals if no modulation of the 1st light source is employed where the $1^{st}$ and $2^{nd}$ pulse is generated as a particle/cell passes through the $1^{st}$ OIZ and the $2^{nd}$ OIZ, respectively; 5C) detected electronic signals when analogue modulations shown in 5A) is applied to the $1^{st}$ light source; 5D) the intermediate de-modulation signal used to recover the $1^{st}$ particle-induced electronic pulse by multiplying the detected electronic signals in 5C) with the modulation sine-wave signal; 5E) recovered $1^{st}$ pulse profile by low-pass filtering the intermediate de-modulation signal in 5D); and 5F) recovered $2^{nd}$ pulse profile by low-pass filtering the detected electronic signals in 5C).

FIG. 6 shows the process of analogue modulation of light sources and de-modulation of electronic signals to recover particle-induced electronic pulse, as a particle/cell passes through three optical interrogation zones: 6A) an analogue signal used to modulate the $1^{st}$ light source (3 MHz); 6B) an analogue signal used to modulate the $3^{rd}$ light source (6 MHz); 6C) detected electronic signals if no modulation of light sources is employed where the $1^{st}$, $2^{nd}$ and $3^{rd}$ pulse is generated as a particle/cell passes through the $1^{st}$ OIZ, the $2^{nd}$ OIZ and the $3^{rd}$ OIZ, respectively; 6D) detected electronic signals when analogue modulations shown in 6A) and 6B) are applied to the $1^{st}$ light source and the $3^{rd}$ light source, respectively; 6E) the intermediate de-modulation signal used to recover the $1^{st}$ particle-induced electronic pulse by multiplying the detected electronic signals in 6D) with the modulation sine-wave signal in 6A); 6F) the intermediate de-modulation signal used to recover the $3^{rd}$ particle-induced electronic pulse by multiplying the detected electronic signals in 6D) with the modulation sine-wave signal in 6B); 6G) recovered the $1^{st}$ pulse profiles by low-pass filtering the intermediate de-modulation signal in 6E); 6H) recovered the $2^{nd}$ pulse profile by low-pass filtering the detected electronic signal in 6D); and 6I) recovered the pulse profile by low-pass filtering the intermediate de-modulation signal in 6F).

FIG. 7 shows the process of analogue modulation of light sources and de-modulation of electronic signals to recover particle-induced electronic pulse, as a particle/cell passes through three optical interrogation zones: 7A) an analogue signal used to modulate the $1^{st}$ and the $3^{rd}$ light source (3 MHz); 7B) detected electronic signals if no modulation of light sources is employed where the $1^{st}$, $2^{nd}$ and $3^{rd}$ pulse is generated as a particle/cell passes through the $1^{st}$ OIZ, the $2^{nd}$ OIZ and the $3^{rd}$ OIZ, respectively; 7C) detected electronic signals when analogue modulation shown in 7A) is applied to both the $1^{st}$ light source and the $3^{rd}$ light source; 7D) the intermediate de-modulation signal used to recover the $1^{st}$ and $3^{rd}$ particle-induced electronic pulse by multiplying the detected electronic signals in 7C) with the modulation sine-wave signal in 7A); 7E) recovered $1^{st}$ and $3^{rd}$ pulse profile by low-pass filtering the intermediate de-modulation signal in 7D); 7F) recovered $1^{st}$ pulse profile through identifying time-window corresponding to particle passing through the $1^{st}$ OIZ; 7G) recovered $2^{nd}$ pulse profile by low-pass filtering the detected electronic signals in 7C); and 7H) recovered $3^{rd}$ pulse profile through identifying time-window corresponding to particle passing through the $3^{rd}$ OIZ. Note that in this example, the same modulation signal is used for modulating the $1^{st}$ and $3^{rd}$ light sources. It is possible to separate, isolate and identify the $1^{st}$ and $3^{rd}$ pulse profiles caused by particle traveling through the $1^{st}$ OIZ and the $3^{rd}$ OIZ, based on identifying appropriate time windows.

DESCRIPTION OF PREFERRED EMBODIMENTS

In one aspect of the invention, a system for detecting signal components of light induced by multiple excitation sources, which includes a flow channel configured for the flow of particles, the flow channel including at least two spatially separated optical interrogation zones; a non-modulating excitation source that directs a light beam of a first wavelength at a near constant intensity onto a first of the optical interrogation zones; a modulating excitation source that directs a light beam of a second wavelength with an intensity modulated over time at a modulating frequency onto a second of the optical interrogation zones, wherein the second wavelength is different from the first wavelength; a detector subsystem comprising a set of detectors configured to detect light emitted from particles flowing through the at least two optical interrogation zones and to convert the detected light into a total electrical signal; and a processor configured to receive the total electrical signal from the detector subsystem, to de-modulate electrical signal that is modulated, and to determine signal components from the light detected from each of the optical interrogation zones.

In an embodiment of the system of the present invention, the system further comprises a third optical interrogation zone spatially separated from the first and second optical interrogation zones; and another excitation source that directs a light beam onto the third optical interrogation zone. In one example of such embodiment, the excitation source that directs the light beam onto the third optical interrogation zone is a second non-modulating excitation source that directs the light beam of a third wavelength at a near constant intensity onto the third optical interrogation zone, wherein the third wavelength is different from both the first wavelength and the second wavelength. In another example of such an embodiment, the excitation source that directs the light beam onto the third optical interrogation zone is a second modulating excitation source that directs the light beam of a third wavelength with an intensity modulated over time at a modulating frequency.

To this end, FIG. 3 describes a preferred embodiment of a flow cytometer system, comprising a light illumination sub-system comprising multiple light sources, at least one of which is intensity-modulated and at least one of which is not modulated and thus provides a constant or near constant intensity, to form multiple optical interrogation zones (OIZs) at different locations along a flow channel, a detection sub-system that detects light emitted from multiple OIZs including light collection optics, light splitters/filters, and photodetectors, an electronic processor sub-system connected to the detection sub-system and capable of isolating and recovering the signal components due to different excitation sources. For preferred embodiments of the present invention, each excitation light source emits light into a single OIZ and different excitation light sources will emit lights into different OIZs.

Preferably, each light source emits a light beam of a different light wavelength to one of at least two, three or more optical interrogation zones. The light wavelengths can be of any values, as long as they are available for exciting fluorescent molecules to be detected for a flow cytometry application. The wavelengths may be selected from ranges centered at about 325 nm, 355 nm, 365 nm, 375 nm, 405 nm, 407 nm, 445 nm, 458 nm, 460 nm, 480 nm, 488 nm, 514 nm, 532 nm, 552 nm, 561 nm, 568 nm, 577 nm, 595 nm, 633 nm, 635 nm, 640 nm, 647 nm, 660 nm, 685 nm, or the like. The term "ranges centered at about" is intended to encompass other neighboring wavelengths as desired, such as about +/−5 nm or as known in the flow cytometry arts.

The light source may be different power levels from as low as a couple of milli-watts to as large as a thousand milli-watts. Preferably, the power of light sources may vary between 2 mW and 1000 mW. More preferably, the power of light sources may vary between 5 mW and 500 mW. Still more preferably, the power of light sources may vary between 10 mW and 200 mW. Even more preferably, the power of light sources may vary between 15 mW and 100 mW. Preferably at least one light beam used for the excitation of fluorescence is intensity modulated and preferably at least one light beam used for the excitation of fluorescence maintains a near constant intensity. By "intensity modulated" it is meant that the intensity (or the power) of the light beam is modulated at a modulating frequency. Approaches to modulate intensity according to a modulating frequency are discussed in detail in sections that follow. In contrast, a beam that maintains a "near constant intensity" refers to a beam that is not modulated and thus retains its intensity or its power without significant deviation throughout the detection or measurement process.

The detector subsystem of the present invention includes a set of detectors for selectively detecting any appropriate wavelengths that are emitted by fluorescent molecules of interest. For instance, a detector subsystem may detect fluorescent wavelength ranges centered at about 421 nm, 450 nm, 455 nm, 519 nm, 530 nm, 578 nm, 585 nm, 603 nm, 615 nm, 620 nm, 650 nm, 660 nm, 785 nm and the like. The examples of detector wavelength ranges may include 421±30 nm, 450±30 nm, 455±40 nm, 519±30 nm, 530±15 nm, 578 n±15 m, 585±40 nm, 603±30 nm, 615±30 nm, 620±30 nm, >650 nm, 660±10 nm, 667±30 nm, 668±30 nm, 678±30 nm, 695±25 nm, >750 nm, 780±30 nm and >785 nm. The fluorescent molecules of interest include, but not limited to those offered under the names PACIFIC BLUE, BD HORIZON V450, DAPI, HOECHST BLUE, ALEXA FLUOR 450, Indo-1 Violet, VIOBLUE, CFP, CLICK-IT EdU PACIFIC BLUE, PO-PRO-1, DYECYLCE Violet, LIVE/DEAD Fixable Violet Dead Cell Stain, Calcein Violet, QDOT 525, AMCYAN, SYTOX Blue, PACIFIC ORANGE, QDOT 565, QDOT 585, LIVE/DEAD Fixable Aqua Dead Cell Stain, QDOT 605, QDOT 655, QDOT 800, Fluorescein, FITC, ALEXA FLUOR 488, QDOT 525, Calcein, FLUO-3 or FLUO-4, TO-PRO-1, CFSE, GFP, EGFP, EYFP, JC-1, $DiOC_2(3)$, $DiIC_2(3)$, SYNTOX Green, DYECYLCE Green, Rhodamine 123, Rhodamine 110, LIVE/DEAD Fixable Green Dead Cell Stain, YO-PRO-1, Indo-1 Blue, CY-2, Acridine Orange, PKH2, BCECF, PI, RPE, ALEXA FLUOR 546, PE-CY5, LP Hoechst Red, PERCP-CY7, FURA RED, DECYCLE Orange, JC-1, $DiOC_2(3)$, SNARF (low pH), PHRODO dye, PE-TEXAS RED, CY3, Pyronin Y, dsRED, PKH26, BCECF, Resorufin RPE-ALEXA FLUOR 610, PI, RPE-TEXAS RED, PI, JC-1, LIVE/DEAD Fixable Red Dead Cell Stain, RPE-ALEXA FLUOR 700, RPE-CY 5.5, TRICOLOR, PERCP, PI, 7-AAD, SNARF (high pH), APC, ALEXA FLUOR 647, Click-iT™ EdU ALEXA FLUOR 647, LIVE/DEAD Fixable Far Red Dead Cell Stain, TO-PRO 3, SYNTOX Red, MITOPROBE DiIC1(5), CELL-TRACE Far Red DDAO-SE RPE-ALEXA FLUOR, ALEXA FLUOR 647, CLICK-IT EdU ALEXA FLUOR 647, CY5, APC CY5.5, DRAQ5, APC-CY7, LIVE/DEAD Fixable Near-IR Dead Cell Stain.

The invention also provides a method of detecting signal components from light induced by multiple excitation sources. The method including: providing a flow channel including at least two spatially separated optical interrogation zones; flowing a population of particles labeled with at least two different fluorescent molecules through each of the optical interrogation zones; directing a light beam of a first wavelength at a near constant intensity onto a first of the optical interrogation zones to induce emission of light from the fluorescence-molecule containing particles; directing a light beam of a first wavelength with an intensity modulated over time according to a modulating frequency onto a second of the optical interrogation zones to induce emission of light from the fluorescence-molecule containing particles, wherein the second wavelength is different from the first wavelength; detecting the light emitted from the particles from each of the optical interrogation zone and converting detected light into a total electrical signal; de-modulating electrical signal from the total electrical; and determining signal components of the light detected from each of the optical interrogation zones.

In some embodiments the method includes flowing the population of particles through a third optical interrogation zone spatially separated from the first and second optical interrogation zones; directing a light beam of a third wavelength at a near constant intensity onto the third optical interrogation zone to induce emission of light from the fluorescence-molecule containing particles, wherein the third wavelength is different from the first and second wavelengths; detecting the light emitted from the particles flowing through the third optical interrogation zone and converting the detected light into the total electrical signal.

In a related embodiment, the method includes flowing the population of particles through a third optical interrogation zone spatially separated from the first and second optical interrogation zones; directing a light beam of a third wavelength with an intensity being modulated over time at the modulating frequency onto the third optical interrogation zone to induce emission of light from the fluorescence-molecule containing particles, wherein the third wavelength is different the first and second wavelengths; and detecting the light emitted from the particles flowing through the third optical interrogation zone and converting the detected light into the total electrical signal.

Thus an exemplary system of the present invention operates in the way described as below. Fluorescent particles/cells are flown through the flow channel and pass through two optical interrogation zones at two different locations along the flow channel. The shaped elliptical laser beams from multiple sources (e.g., S1, S2 in FIG. 3) of different wavelengths propagate across the flow channel and form two optical interrogation zones (OIZ1 and OIZ2) at different vertical locations along the flow channel. When a particle/cell flows through the flow channel, it will pass the individual OIZ (e.g. OIZ1 corresponding to laser beam S1 and OIZ2 corresponding to laser beam S2 in FIG. 3) in sequence. Consequently, fluorescent light will be emitted in sequence as well by different fluorescent molecules (FM) possessed by the particle/cell. In prior art as shown in FIG. 1, light from two locations is collected and further optically/physically separated to two different positions separated in a distance large enough to physically accommodate optical filters and detectors in order to detect the signals. However, in the present invention, light from multiple locations (e.g. two locations in FIG. 3) is collected using collection optics but does not need to be further separated. Collected light is then split into different components covering different wavelength ranges of the light spectrum using splitters and filters. Each light component covering a wavelength range is detected by a photodetector to output an electronic signal. As particles/cells flow through in the flow channel, each particle/cell generates one light-scatter-induced electronic pulse and one or multiple fluorescence-induced electronic pulse dependent on the fluorochrome labeling of the particle/cell as it passes through each OIZ.

If the emission light of the two different FMs excited by different excitation light source are not the same or do not overlap, then fluorescent light emitted by these two FMs will be detected separately by two different photodetectors covering different wavelength ranges. On the other hand, if the emission spectra of two FMs are the same or overlapped, the fluorescent light from the two types of FMs will be detected by same photodetectors. The isolation/recovery of the fluorescent light component due to either type of FMs is achieved through modulation of light sources and de-modulation of the electronic signals. In one example, both light sources are intensity-modulated with each source modulated at a same unique frequency. In a preferred embodiment, one light source is intensity-modulated at a certain frequency and the other light source is not modulated. Below we discuss these two exemplary approaches.

In one exemplary embodiment, for FIG. 3A, the $1^{st}$ excitation light source having the $1^{st}$ wavelength is modulated at one frequency whilst the $2^{nd}$ light source having the $2^{nd}$ wavelength is modulated at another frequency. Thus, resulting fluorescent signals (FS1 and FS2 in FIG. 3A) excited by the $1^{st}$ excitation light source and the $2^{nd}$ excitation light source as the particle/cell passes through the two OIZs (OIZ1 and OIZ2) and their corresponding electronic signals from photodetectors are also modulated at two corresponding frequencies. Modulated electronic signals due to each light source can be de-modulated separately to recover the pulse profile through certain modulation-frequency-dependent electronic signal processing means. Thus, it is possible to isolate and detect fluorescent light from each type of fluorescent signals excited by two different light sources. As an example in FIG. 3A, S1 can be 488 nm laser and S2 can be 640 nm laser. Fluorescent molecules FITC and PE-Cy7 can be excited by S1 (488 nm) and emit light at peak wavelength of 519 nm and 785 nm respectively whilst APC and APC-Cy7 can be excited by S2 (640 nm) and emit light at peak wavelength of 660 nm and 785 nm respectively. FS1 may comprise fluorescent signals from two fluorescent molecules FM1 (e.g., FITC) and FM2 (e.g., PE-Cy7) and FS2 may comprise fluorescent signals from two fluorescent molecules FM3 (e.g., FITC) and FM4 (e.g., PE-Cy7). Both FS1 and FS2 are collected together through collection optics and are then split in three different wavelength ranges peaked at 519 nm (from FM1: FITC), 660 nm (from FM3: APC) and 785 nm (from FM2: PE-Cy7) and FM4: APC-Cy7) and detected by three photodetectors D1, D2 and D3, respectively. The electronic signals from photodetectors are processed via electronics processor to derive four output signals E1, E2, E3 and E4, corresponding fluorescent signals form FM1, FM2, FM3 and FM4, respectively. Specifically, relating to the overlapped emission spectra from FM2 and FM4, the photo-detector D3 converts fluorescent signals peaked at 785 nm from FM2 and FM4 into a combined electronic signal. To separate signal components, light sources S1 and S2 are modulated at two different frequencies. Thus, the electronic signal components corresponding to FM2 and FM4 are modulated at different frequencies. Using the electronics processor, these modulated electronic signals are de-modulated to derive electronic signals corresponding to each type of fluorescent molecules FM2 and FM4.

In yet a preferred embodiment, for FIG. 3A, the $1^{st}$ excitation light source S1 having the $1^{st}$ wavelength is not modulated whilst the $2^{nd}$ light source S2 having the $2^{nd}$ wavelength is modulated at a certain frequency. Thus, resulting fluorescent signal FS1 and resulting scattered laser light signal in FIG. 3A excited by the $1^{st}$ excitation light source as the particle/cell passes through OIZ1 and the corresponding electronic signals from photodetectors are not intensity modulated. Such non-modulated electronic signals would be in the form of a pulse profile with time. On the other hand, resulting fluorescent signal FS2 in FIG. 3A excited by the $2^{nd}$ excitation light source as the particle/cell passes through OIZ2 and the corresponding electronic signals from photodetectors are modulated at the same frequency as that of modulation for the $2^{nd}$ light source. Such modulated electronic signals due to the $2^{nd}$ light source can be de-modulated separately to recover the pulse profile through certain modulation-frequency-dependent electronic signal processing means. Because of spatial separation of OIZ1 and OIZ2, there is a time difference between the two pulse profiles, one directly obtained from photodetectors due to the $1^{st}$ excitation light and another recovered through demodulation of the modulated electronic signals from photodetectors due to the $2^{nd}$ excitation light. Such time difference is dependent on spatial distance of OIZ1 and OIZ2, and on the travel speed of particle/cell in the flow cell. Thus, it is possible to isolate and detect fluorescent light from each type of fluorescent signals excited by two different light sources. As an example in FIG. 3A, S1 can be 488 nm laser and S2 can be 640 nm laser. Fluorescent molecules FITC and PE-Cy7 can be excited by S1 (488 nm) and emit light at peak wavelength of 519 nm and 785 nm respectively whilst APC and APC-Cy7 can be excited by S2 (640 nm) and emit light at peak wavelength of 660 nm and 785 nm respectively. FS1 may comprise fluorescent signals from two fluorescent molecules FM1 (e.g., FITC) and FM2 (e.g., PE-Cy7) and FS2 may comprise fluorescent signals from two fluorescent molecules FM3 (e.g., FITC) and FM4 (e.g., PE-Cy7). Both FS1 and FS2 are collected together through collection optics and are then split in three different wavelength ranges peaked at 519 nm (from FM1: FITC), 660 nm (from FM3: APC) and 785 nm (from FM2: PE-Cy7) and FM4: APC-Cy7) and detected by a set of three photodetectors D1, D2 and D3, respectively. The electronic signals from photodetectors are processed via electronics processor to derive four output signals E1, E2, E3 and E4, corresponding fluorescent signals form FM1, FM2, FM3 and FM4, respectively. Specifically, relating to the overlapped emission spectra from FM2 and FM4, the photo-detector D3 converts fluorescent signals peaked at 785 nm from FM2 and FM4 into a combined electronic signal. To separate signal components, light sources S1 is not intensity modulated and light source S2 is intensity modulated at a certain frequency. Thus, the electronic signal component corresponding to FM2 is not modulated and can be obtained after straightforward signal processing such as amplification and low-pass filtering on the signals directly from the photodetector. The electronic signal component corresponding to FM4 is modulated at the frequency of modulation for light source S2 and such modulated electronic signals are de-modulated to derive electronic signals corresponding to fluorescent molecule FM4. Examples of de-modulation approaches will be described in the following sections.

There are several advantages of this preferred embodiment where one light source is not modulated and another light source is modulated, comparing to the case of both light sources are modulated. First, as particle/cell passes through OIZ1 where the $1^{st}$ light source is not modulated, the particle scattered light signals (both forward scatter and side scatter signals) are also not modulated and would be in the form of a pulse-profile. Such particle scattered pulse profiles can be directly-used for determining appropriate time window for corresponding fluorescent signals due to the $1^{st}$ light source, and for determining appropriate time windows for fluorescent signals due to the $2^{nd}$ light source after taking into account of the spatial distance between OIZ1 and OIZ2 and the travel speed of particle/cell in the flow cell. Use of such particle-scattering signals as a time window for fluorescent signals is beneficial to filter out unwanted noises in fluorescent detection channels. Also, particle scattering signals depends on primarily on particle size, shape and surface scattering properties and do not rely on presence of fluorescent molecules in the particle. Thus, particle scattering signals can be reliably obtained even if the particle fluorescent signals are low. If the $1^{st}$ light source is modulated, then such particle scattered signals would also be modulated. The modulated scatter signals could not be used directed for determining the corresponding time window for fluorescent signals. Thus, one would need to first de-modulated the modulated scatted signals to recover the scatter-signal pulse profile. Such approach would lead to complex procedures in processing various signals. It's much more preferred to have $1^{st}$ light source un-modulated and use its corresponding scatted signal to determine fluorescent signal windows. Secondly, fluorescent signals and corresponding electronic signals due to the $1^{st}$ light source are not modulated, avoiding the need of de-modulation steps or processes for recovering the corresponding electronic pulse profiles. This is beneficial to reducing over system complexity involved in signal processing. Without the need for demodulation of fluorescent signals and scattered signals due to the $1^{st}$ light sources, more system resources could be employed for processing fluorescent signals due to the $2^{nd}$ light source, potentially improving signal to noise ratio for such channels. Thirdly, since one light source is modulated, choice of suitable modulation frequency would be more straightforward, compared with the case where two light sources are modulated at two different modulation frequencies.

The light illumination sub-system comprises multiple light sources used to excite fluorescent molecules (FM) when a particle/cell flows through the flow channel. In the example of FIG. 3A, two excitation light sources S1, S2 having different wavelengths are used. During operation, it is preferred that one light source S1 is not modulated and thus maintains a constant intensity at the flow channel and one light source S2 is intensity-modulated.

Figure 3B:
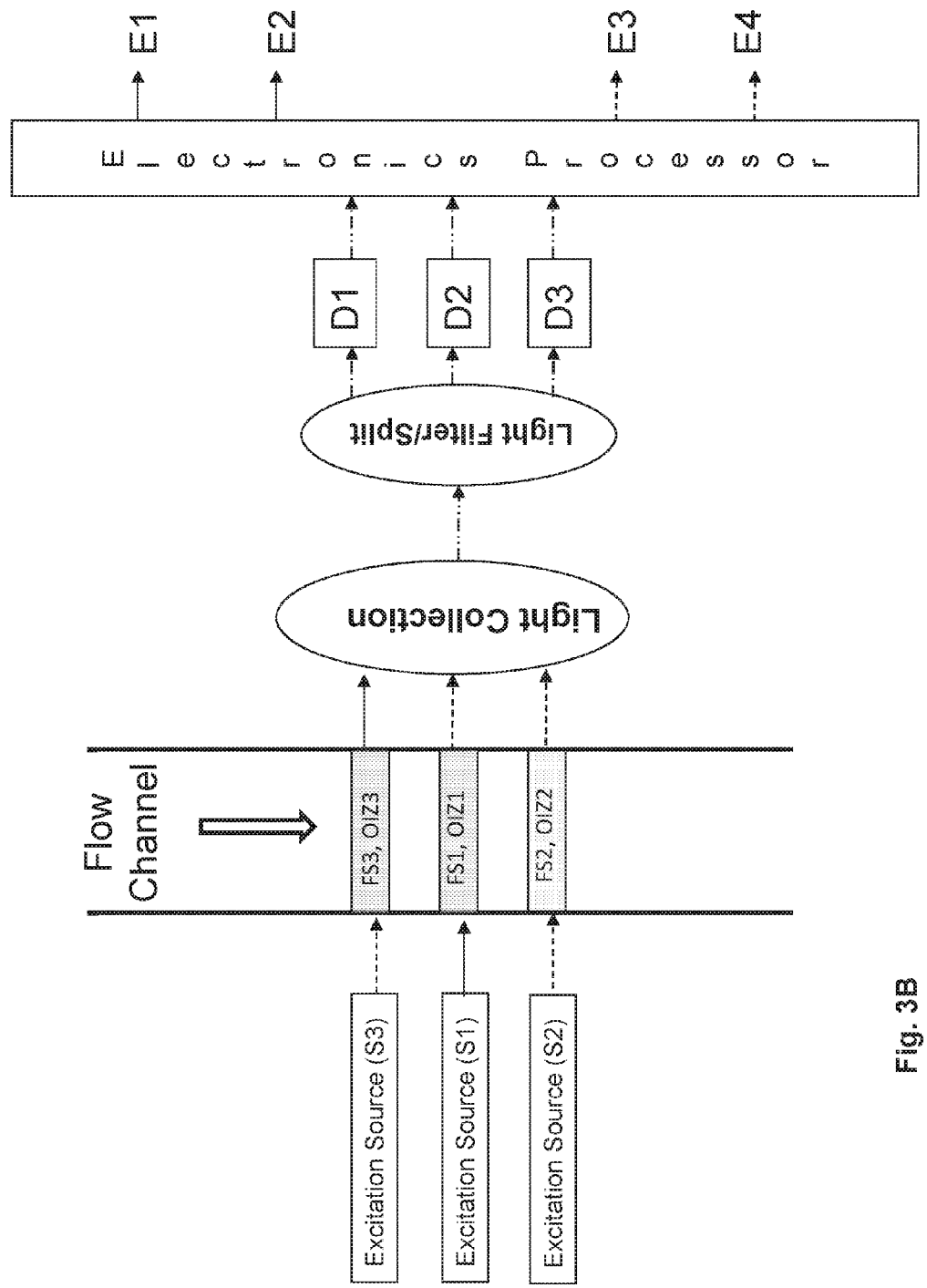
FIG. 3B shows an exemplary schematic representation of the present invention where a light illumination sub-system directs light beams from two excitation light sources S1, S2, S3 to three optical interrogation zones OIZ1, OIZ2, OIZ3, separated at some distances along the flow channel. Light emitted from the two OIZs (FIG. 3A) or three OIZs (FIG. 3B) is collected using same light collection optics. The collected light is then split or filtered into light components of different wavelength ranges and is detected by a set of photodetectors. The electronic signals from photodetectors are processed using electronics processor.

In another embodiment of the invention, three excitation light sources having different wavelengths can be used. In a preferred embodiment, at least one light source is not modulated and at least one light source is intensity-modulated. For example, in one embodiment, one light source is intensity-modulated and the other two light sources are not modulated. For such an embodiment, the light beams from the three light sources may be arranged along the flow cell in such an order that the modulated light beam is positioned in the middle with the two un-modulated light beams positioned each at one side (or end) of the modulated beam along the flow cell. As shown in FIG. 3B, in another embodiment, one light source S1 is not modulated and the other two light sources S2, S3 are intensity-modulated. For such an embodiment, the light beams from the three light sources S1, S2, S3 may be arranged along the flow cell in such an order that the un-modulated light beam is positioned in the middle with the two modulated light beams positioned each at one side (or end) of the un-modulated beam along the flow cell. The modulation frequencies of two intensity-modulated light sources S2, S3 may be different. In preferred embodiments, the modulation frequencies of two intensity-modulated light sources S2, S3 are the same. Since there are spatial distances between light beams from the three different light sources S1, S2, S3 along the flow direction of the flow cell, fluorescent signals caused by each light source S1, S2, S3 would occur at different time windows as particle/cell travel through three different optical interrogation zones OIZ1 OIZ2, OIZ3. By taking advantage of such time differences among fluorescent signal pulse profiles due to different light sources, two of the modulated light sources S2, S3 may employ the same modulation frequency. This way, the same modulation signals can be used to modulate both light sources S2, S3, simplifying the system design. Furthermore, the same de-modulation processor or circuits can be used to de-modulate the fluorescence-corresponding electronic signals from both modulated light sources S2, S3. This would significantly reduce the system hardware/software complexity and improve system reliability and performance. Thus, there are important benefits and advantages with using a same modulation frequency for light sources being modulated, compared with the embodiments where different modulation frequencies are used for the two modulated light sources. In addition, for the embodiments of the present invention where three light sources S1, S2, S3 having different light wavelengths are used, there are important advantages having one light source S1 not modulated. The advantages described above for two light sources where one light source is not modulated can be applied to three light sources embodiments described in this paragraph.

In still another embodiment of the invention, four excitation light sources having different wavelengths can be used. In still another embodiment of the invention, five excitation light sources having different wavelengths can be used. During operation, at least one light source is not modulated and at least one light source is intensity-modulated. For example, in one embodiment, two light sources are intensity-modulated and the other two light sources are not modulated. For such an embodiment, the light beams from the four light sources may be arranged along the flow cell in such an order that the un-modulated light beam and modulated light team are positioned in an alternative manner. The modulation frequencies of two intensity-modulated light sources may be different. In certain preferred embodiment, the modulation frequencies of two intensity-modulated light sources are the same. For such preferred embodiment of using the same modulation frequency for two intensity-modulated light sources, the advantages and benefits described for using a same modulation frequency for two modulated light sources in above paragraph for three light source embodiments are also applicable here. In addition, for the embodiments where four light sources having different light wavelengths are used, there are important advantages having one light source not modulated. The advantages described above for two light sources where one light source is not modulated can be applied to four light sources embodiments described in this paragraph.

In the present invention, at least one of the multiple light sources can be modulated and at least one of the multiple light sources is not modulated. For N light sources (N is the number of multiple light sources with different wavelength), some light sources can be modulated and other light sources are not-modulated. Preferably, light beams from these light sources may be arranged along the flow cell in such an order that the un-modulated light beam and modulated light team are positioned in an alternative manner. The modulation frequencies of those intensity-modulated light sources may be different. In certain preferred embodiment, the modulation frequencies of the intensity-modulated light sources are the same. For such N-light source cases, the advantages and benefits described in previous paragraphs associated with having one light source not-modulated or with having same modulation frequencies for two modulated light sources are also applicable here.

Different methods can be used to modulate light sources, including digital modulation and analogue modulation. For digital modulation, light from the light source can be turned on or off by the digital signals used for digital modulation with certain modulation ratio (the ratio of ON-light intensity to OFF-light intensity). Preferably, the digital modulation ratio is larger than 10. More preferably, the digital modulation ratio is larger than 100. For many practical light sources (e.g. lasers), digital modulation could not achieve a true OFF of light source. Thus, digital modulation is a special case of light-intensity modulation. In analogue modulation, light intensity from the light source can be controlled to be proportional to the amplitude of the analogue signals used for analogue modulation. The analogue signals used for modulation can be of different waveforms, including sine-waveform, triangular-waveform, and seesaw-waveform. The light source can be modulated at any suitable frequencies, as long as the modulated particle-induced electronic pulses can be de-modulated through electronics-processing means to recover the particle-induced electronic pulses.

The modulation frequency could be in various ranges, typically MHz, from less than 0.1 MHz to 10 MHz, even above 100 MHz. The modulation frequency depends on a number of factors, including how fast the particles/cells are flowing through the flow channel, up to what frequency ranges the light source could be possibly modulated and what de-modulation means is used to recover particle-induced electronic pulses. For example, if the particle/cell flow rate in the flow channel is such that it takes about one to several micro-seconds for a particle/cell to go through one OIZ, then the modulation frequency could be in the range of several MHz or above. On the other hand, if the particle/cell flow rate is slow and it takes about 10 micro-seconds or more for a particle/cell to go through one OIZ, then the modulation frequency could be in the range of 1 MHz or above. High modulation frequency could be used as long as it is within modulation frequency range of the light source and as long as the modulated signals could be de-modulated through electronics-processing means. Preferably, the modulation frequency is between 0.1 MHz and 100 MHz. More preferably, the modulation frequency is between 1 MHz and 20 MHz. Even more preferably, the modulation frequency is between 2 MHz and 10 MHz. Even more preferably, the modulation frequency is between 3 MHz and 8 MHz.

The light illumination sub-system is constructed so that multiple light beams of different wavelengths having appropriate geometrical shapes (e.g. elliptical shape, rectangular shape) are directed to multiple OIZs at different locations along the flow direction of the flow channel. That is to say, adjacent optical interrogation zones (or adjacent light beams of different wavelengths) do not overlap in the flow channel. To define the separation between adjacent optical interrogation zones, the center-to-center distance between adjacent optical interrogation zones is used. Such a center-to-center distance between adjacent OIZs could be of different values. The center-to-center distance could be as large as more than 500 microns. The center-to-center distance between adjacent light beams depends on a number of factors including the minor axis of light beams along the flow direction at OIZs, the light collection efficiency for light emitted from different OIZs, the flow speed range of particles/cells flowing inside the flow channel and the particle/cell concentration range. For the present invention, single light-collection-optics set is used to collect light from multiple OIZs at different locations along the flow channel, light collection efficiency may differ for light emitted from different OIZs For example, light-collection-optics may include an objective lens or lens set. The light collection efficiency may be low for collecting light from OIZs far away from the central axis of the objective lens or lens set. Thus, the center-to-center distance between adjacent OIZs should not be too large so that light collection efficiency for light emitted from any OIZs is not too low. In addition, a large center-to-center distance between adjacent OIZs increases the probability of two particles/cells passing through two adjacent OIZs simultaneously, especially when particle/cell concentration is high. Thus, preferably, at any given moment, there should be one or zero particle/cell passing through either one of two adjacent optical interrogation zones in the present invention. On the other hand, preferably, the light beams at adjacent OIZs do not overlap. For example, if the excitation beam has an elliptical shape whose minor axis is 15 microns parallel to the flow direction, the center-to-center distance between adjacent OIZs is preferably between 15 microns and 150 microns, leaving the gap between the adjacent light beams propagating through the flow cells in the range of 0 to 135 microns. In one embodiment, if the center-to-center distance is 30 microns for such 15 micron minor axis beams, then the gap between the adjacent light beams is 15 microns.

In one preferred embodiment, light beams illuminated to the OIZs have a minor axis of about 10 microns. In such an embodiment, preferably, the center-to-center distance between adjacent optical interrogation zones along the flow direction is between 10 micros and 300 microns. Even more preferably, the center-to-center distance between adjacent optical interrogation zones along the flow direction is between 20 microns and 200 microns. Still more preferably, the center-to-center distance between adjacent optical interrogation zones along the flow direction is between 25 microns and 100 microns. Still more preferably, the center-to-center distance between adjacent optical interrogation zones along the flow direction is between 30 microns and 80 microns. Still more preferably, the center-to-center distance between adjacent optical interrogation zones along the flow direction is between 35 microns and 70 microns. Note that for light beams having 10 micron as minor axis along the flow direction, the center-to-center distance of 20 microns mean that there is no gap between the two adjacent optical-detection-zones and the distance of 50 microns means that the gap between the two adjacent optical-detection-zones is 30 microns. The light illumination sub-system of the present invention may include beam-steering and/or beam combining and/or light focusing and/or or other optical components to deliver light beams to different locations along the flow channel.

Light source system may include components capable of generating light such as laser, light-emitting diodes (LED) or other sources. It may also include light beam shaping and beam steering optical components. Those who are skilled in the art of light beam shaping can readily design different beam shaping optic components and sub-system to shape the light from the source to desired shape, typically an elliptical or nearly-rectangular shape. Various methods could be used for steering light or directing light to multiple optical interrogation zones at different locations along the flow channel.

Particles/cells to be detected or measured are suspended in a liquid and particle/cell suspension would be flown through the flow channel and driven into the central region of the flow channel under hydrodynamic focusing or other focusing forces. When the focused particles/cells pass through each optical interrogation zone, fluorescent molecules within the particles/cells are excited by light beams in the OIZ and produce transient fluorescent light pulses. Similarly, there are also particle-scatter-light-induced pulses as particles/cells go through an OIZ. At the detection side of each channel, the particle-induced electronic signal correlated with particle fluorescent intensity and particle scatter light intensity is generated using a photodetector such as PMT, APD or the like.

Fluorescent light emitted from multiple optical interrogation zones (OIZ1 and OIZ2 FIG. 3) can be collected via various optical components. Those who are skilled in optical design of flow cytometer and/or in optical design for light collection could readily design/develop a suitable optical collection sub-system for efficient collection of light. Among other components, such optical collection sub-system may include optical components such as light-splitting components based on light wavelengths, such as dichroic mirrors, band-pass filters, low-pass filters and/or high-pass filters, photodetectors such as PMT, APD or the like. A critical difference from the first approach in prior art (as illustrated in FIG. 1) is that in present invention, there is no need for optical collection sub-system to physically/optically separate light from different optical interrogation zones to different locations. That is, optical collection components can be shared between OIZs due to the intensity modulation approach of the invention. Collected light is then split or filtered so that light of various wavelength ranges is separated and detected by photodetectors such as PMT or APD or the like. Furthermore, for the present invention, light splitting optics including components such as dichroic mirrors and band-pass filters can also be shared for detecting light emitted from different OIZs.

The electronic output from photodetectors is then processed electronically. The electronic signals from each channel (i.e. a fixed wavelength range signal) may have multiple components since the light is emitted from multiple OIZs at different locations along the flow channel. For example, the electronic signals will contain two components since light emitted from two OIZs are mixed together and collected together using the same light-collection optics. If different types of fluorescent molecules being excited at different OIZs by light sources of different wavelengths do not have the same emission spectra (i.e. detection wavelength ranges for theses FMs do not overlap), the isolation of electronic pulses for different fluorescent molecules is possible since light of different wavelengths is detected by different photodetectors (i.e. different detection channel). On the other hand, if different types of fluorescent molecules being excited at different OIZs by light sources of different wavelengths have the same emission spectra (i.e. detection wavelength ranges for these FMs are the overlapped), the isolation of electronic pulses for different fluorescent molecules is still possible through de-modulation of the modulated electronic signals from photodetectors. The isolation of electronic pulses for different fluorescent molecules excited at different OIZs by light sources of different wavelengths may also be achieved through exploiting the time differences of these electronic pulse profiles. Such time differences are dependent on spatial distances between two OIZs of interest, and on the travel speed of particle/cell in the flow cell. Therefore, the same set of filters and photodetector could be shared for detection of emitted light with the same/overlapped emission spectra but excited by different light sources.

EXAMPLE 1

Two Intensity-Modulated Light Sources

Below we will discuss some examples of modulation and de-modulation methods. For example, light beam directed to OIZ1 is modulated by a sine-wave signal at a frequency $f_1$ and phase value zero (i.e. Mod1=$\sin(2\pi f_1 t)+1$) and light beam directed to OIZ2 is modulated by a sine-wave signal at a frequency $f_2$ and a phase value $\phi_2$ (i.e. Mod2=$\sin(2\pi f_2 t+\phi_2)+1$)). The first modulation signal Mod1 has a phase value of zero and its phase is used as a reference for all signals in the system. Thus, the second modulation signal Mod2 has a phase value of $\phi_2$. Total electronic signals Total_Signal from a photodetector is the sum of the signal associated with emitted light from OIZ1 (Sig1) and OIZ2 (Sig2), respectively, and can be expressed as, $$Total_{Signal} = Sig1 + Sig2 \qquad (1)$$
$$= S_1(t)(\sin(2\pi f_1 t + \varphi_3) + 1) + S_2(t)(\sin(2\pi f_2 t + \varphi_4) + 1)$$

where $S_1(t)$ and $S_2(t)$ are output electronic signal from the photodetector due to particles/cells passing through the $1^{st}$ OIZ and the $2^{nd}$ OIZ, respectively, when no modulation is applied to either one of the light sources. Note that in equation (1), the electronic signals from the photodetector have phase values $\phi_3$ and $\phi_4$, in comparison with phase values of zero and $\phi_2$ of the modulation signals. The factors contributing to such a phase change (or phase difference) include the response-time-delay of light source between the modulation electronic signals and the modulated light beams at OIZs, the response time or relaxation time or life time of fluorescent molecules, and the response time of photodetectors, and other possible time delays within the system from modulation of light sources to detecting fluorescent signals on the photodetectors. U.S. Pat. Nos. 5,196,709 and 5,270,548 described the method and apparatus capable of measuring the life time of fluorescent molecules; the methods of which are herein incorporated by reference. For the present invention, an electronic processor is used to de-modulate the Total_Signal to recover electronic signal $S_1(t)$ and $S_2(t)$ so that the light intensity (i.e. fluorescence or side-scatter) can be derived at the corresponding detection channel.

Different methods may be used for the de-modulation. Below, we will consider two approaches. In the first approach as illustrated later, we do not take into account the phase differences between the modulation signals applied to excitation light beams and the electronic signals from the photodetector. In another word, it is assumed that there is no phase change or phase difference for the electronic signals from the photodetector, relative to the phase values of the modulation signals. Such a first approach is called "one-component de-modulation". In the second approach, we consider the phase differences between the modulation signals applied to excitation light beams and the electronic signals from the photodetector. Such a second approach is called "quadrature modulation".

One-Component De-Modulation

For the first approach of "one-component de-modulation" where the phase difference between the electronic signals from photodetector and the modulation signals is not considered, total electronic signals Total_Signal from a photodetector in equation (1) can be expressed as $$\text{Total}_{Signal} = Sig1 + Sig2 \quad (2)$$
$$= S_1(t)(\sin(2\pi f_1 t) + 1) + S_2(t)(\sin(2\pi f_2 t + \varphi_2) + 1).$$

In order to recover $S_1(t)$, we would multiply Total_Signal with its corresponding modulation signal $\sin(2\pi f_1 t)$, then we have $$\text{Intermediate\_Signal} = \text{Total\_Signal} * \sin(2\pi f_1 t) \quad (3)$$
$$= S_1(t)\sin(2\pi f_1 t) * \sin(2\pi f_1 t) + S_1(t)\sin(2\pi f_1 t) +$$
$$S_2(t)\sin(2\pi f_2 t + \varphi_2) * \sin(2\pi f_1 t) +$$
$$S_2(t)\sin(2\pi f_1 t)$$
$$= 0.5 S_1(t) - 0.5 S_1(t)\cos(4\pi f_1 t) + S_1(t)\sin(2\pi f_1 t) +$$
$$0.5 S_2(t)\cos(2\pi(f_2 t - f_1 t) + \varphi_2) -$$
$$0.5 S_2(t)\cos(2\pi(f_2 t + f_1 t) + \varphi_2) + S_2(t)\sin(2\pi f_1 t)$$

Thus, the above Intermediate_Signal has multiple components, including a term $S_1(t)$, and other terms with $S_1(t)$ and $S_2(t)$ being modulated with sine-wave or cosine-wave forms at different frequencies of $f_1$, $2f_1$, $(f_1+f_2)$ or $|f_1-f_2|$. In order to recover $S_1(t)$ from Intermediate_Signal, we analyze the signal in terms of its frequency spectra. Depending on the linear velocity of a particle/cell flowing through the flow channel (typically, <10 m/sec) as well as the beam size (10~20 microns), the time taken for a particle to pass through the optical detection zone could vary from ~1 micro-second to more than 1 micron-second, leading to the frequency bandwidth of the particle-induced electronic pulse signal $S_1(t)$ or $S_2(t)$ being estimated as between 0 and 1 MHz (or even between 0 and 0.5 MHz). Thus, the six component terms in the Intermediate_Signal of equation (2) have signal bandwidths between 0 and 1 MHz, between $2f_1$ and $(2f_1+1)$ MHz, between $f_1$ and $(f_1+1)$ MHz, between $|f_1-f_2|$ and $|f_1-f_2|+1$ MHz, between $(f_2+f_1)$ and $(f_2+f_1)+1$ MHz, and between $f_1$ and $(f_1+1)$ MHz, respectively. Under these conditions, the modulation frequency is preferably to be higher than 2-times of the signal frequency bandwidth, i.e., above 2 MHz. In addition, the difference between two modulation frequencies is also preferably to be higher than 2-time of the signal frequency bandwidth. In one example, $f_1$ and $f_2$ could be 6 MHz and 3 MHz, respectively. In another example, $f_1$ and $f_2$ could be 10 MHz and 4 MHz, respectively. Under these conditions, particle-induced electronic pulse signal $S_1(t)$ could be recovered by filtering the Intermediate_Signal through a low-pass filter with a cut-off frequency at ~1 MHz. Therefore, except the $1^{st}$ term, all the other terms in equation (2) would be filtered out by the low-pass filter, thus recover signal $S_1(t)$ from the Intermediate_Signal. Generally speaking, in order to recover signal $S_1(t)$ from the Intermediate_Signal in equation (3), the modulation frequencies of $f_1$ and $f_2$ must be chosen so that the values of $f_1$, $2f_1$, $(f_1+f_2)$ and $|f_1-f_2|$ should be all above the frequency bandwidth of the signal $S_1(t)$. Preferably, the modulation frequencies of $f_1$ and $f_2$ must be chosen so that the values of $f_1$ and $|f_1-f_2|$ are at least two-times of the frequency bandwidth of the signal $S_1(t)$.

Figure 4A:
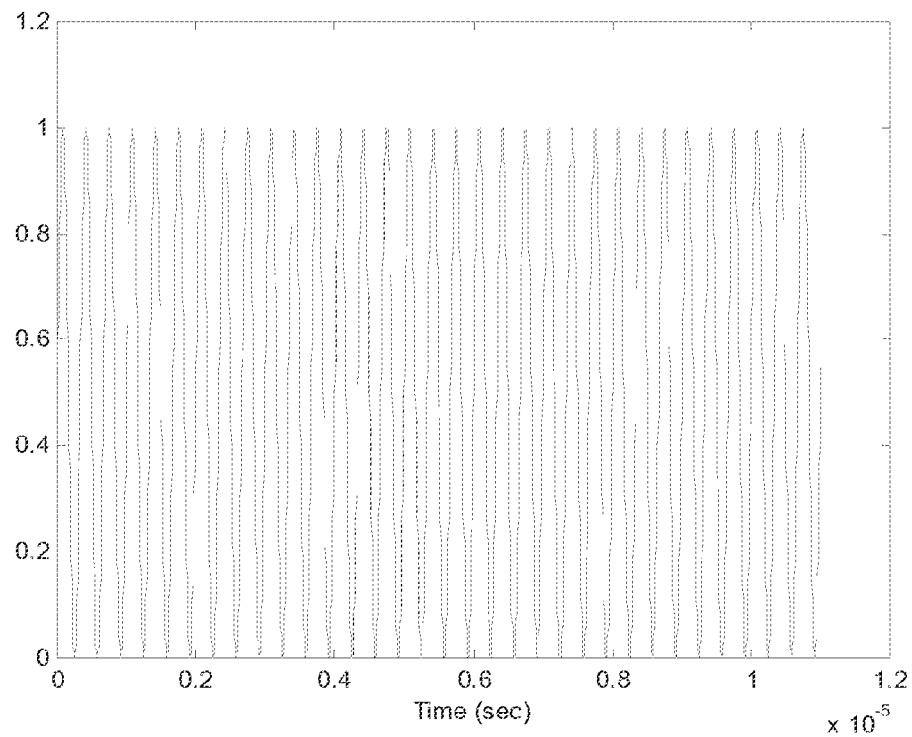
FIG. 4 shows the process of analogue modulation of light sources and de-modulation of electronic signals to recover particle-induced electronic pulse, as a particle/cell passes through two optical interrogation zones: 4A) an analogue signal used to modulate the $1^{st}$ light source (3 MHz); 4B) an analogue signal used to modulate the $2^{nd}$ light source (6 MHz); 4C) detected electronic signals if no modulation of either light source is employed where the $1^{st}$ and $2^{nd}$ pulse is generated as a particle/cell passes through the $1^{st}$ OIZ and the $2^{nd}$ OIZ, respectively; 4D) detected electronic signals when analogue modulations shown in 4A) and 4B) are applied to the $1^{st}$ light source and the $2^{nd}$ light source, respectively; 4E) the intermediate de-modulation signal used to recover the $1^{st}$ particle-induced electronic pulse; 4F)
Figure 4B:
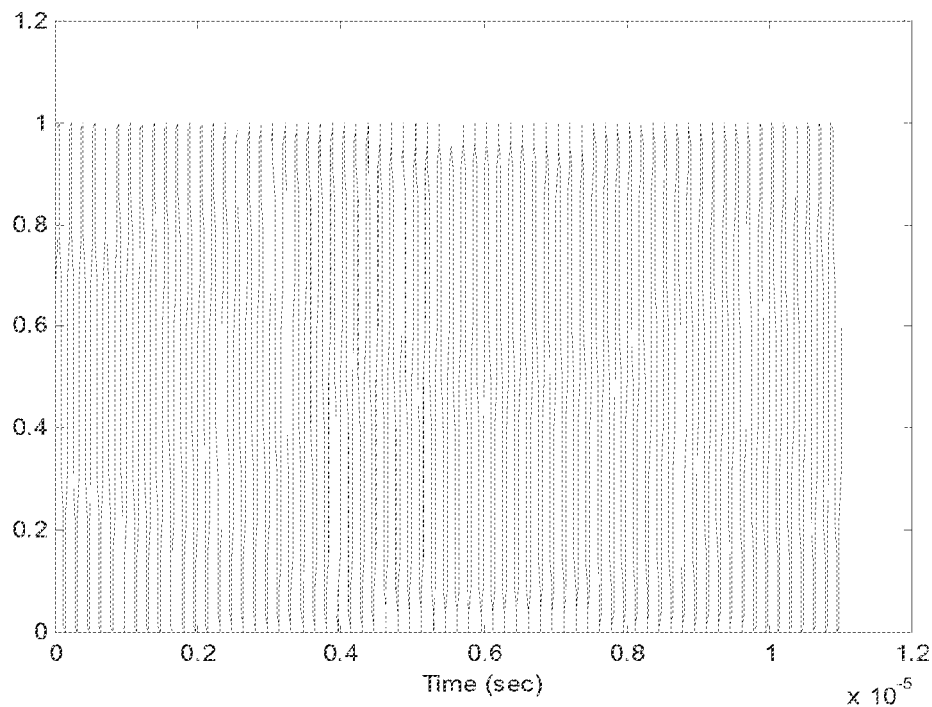
Figure 4C:
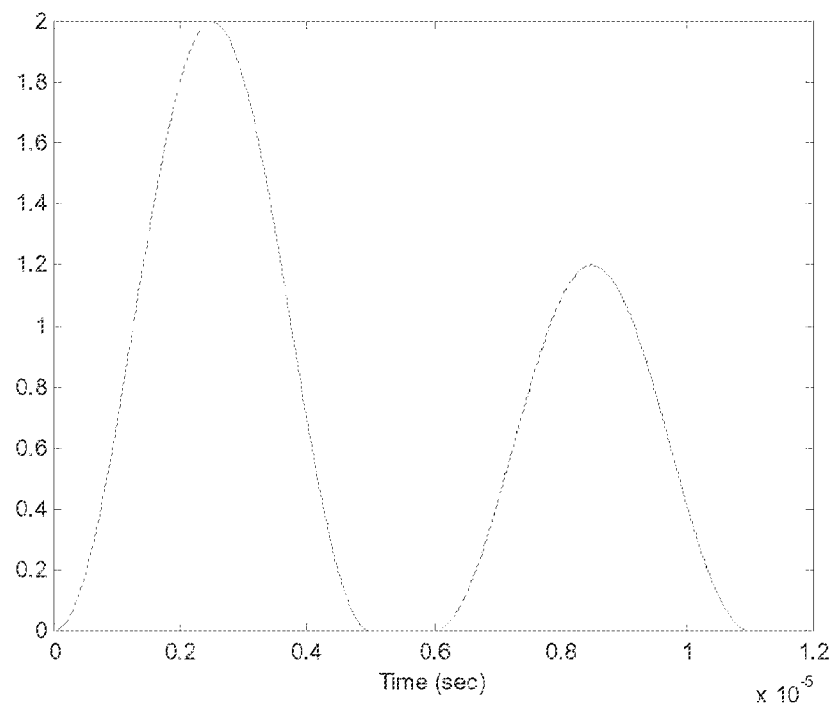
Figure 4D:
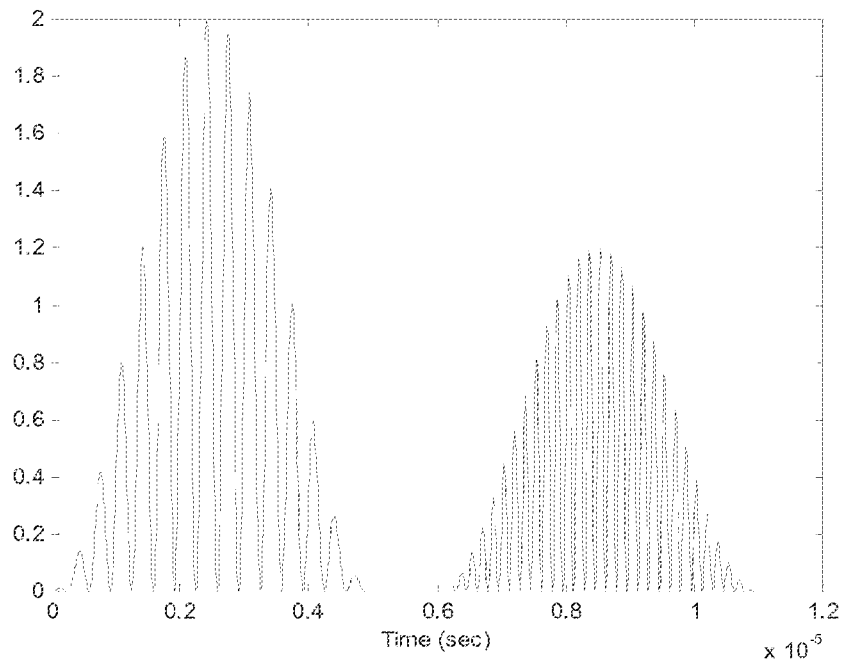
Figure 4E:
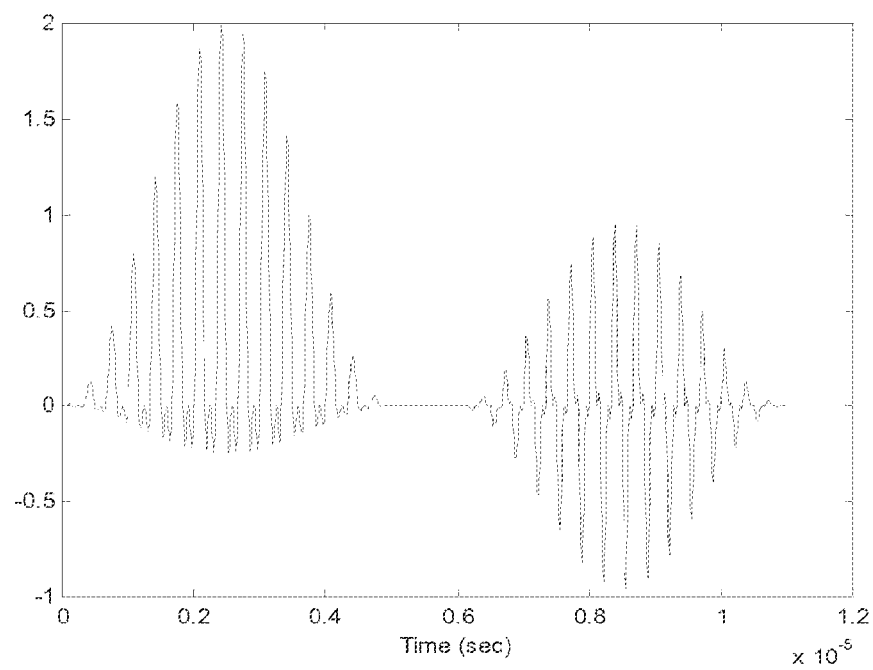
Figure 4F:
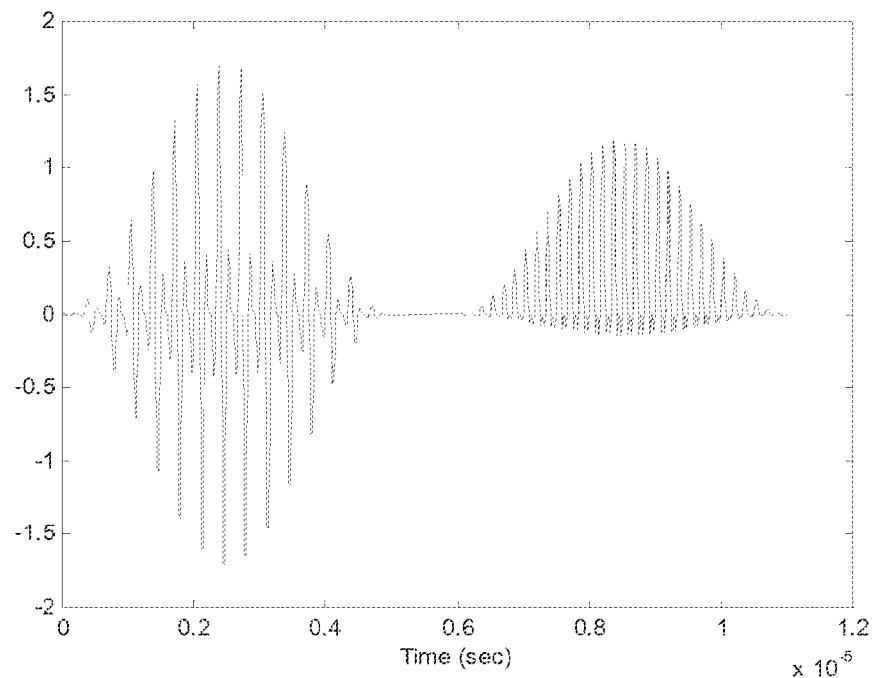
Figure 4G:
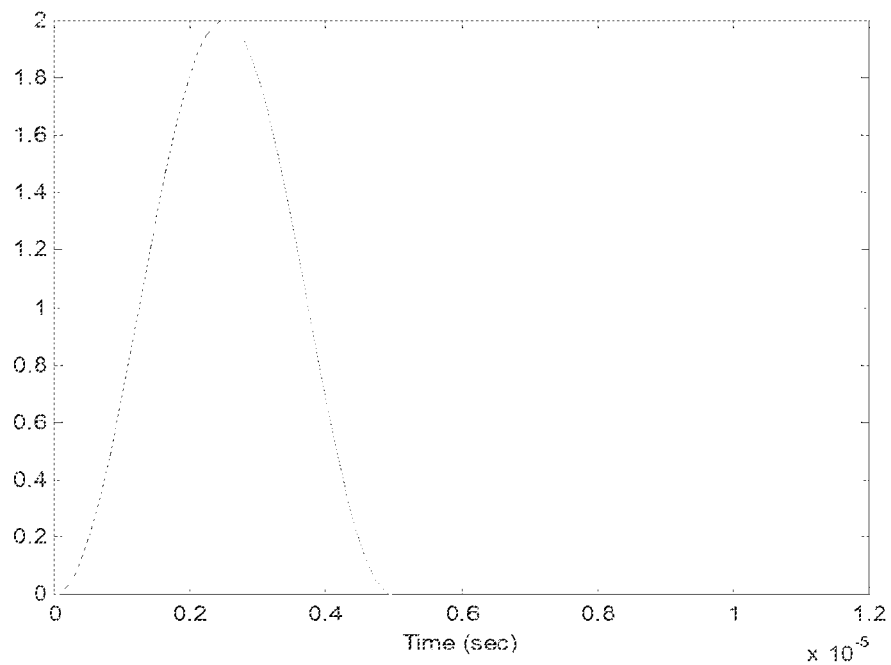
Figure 4H:
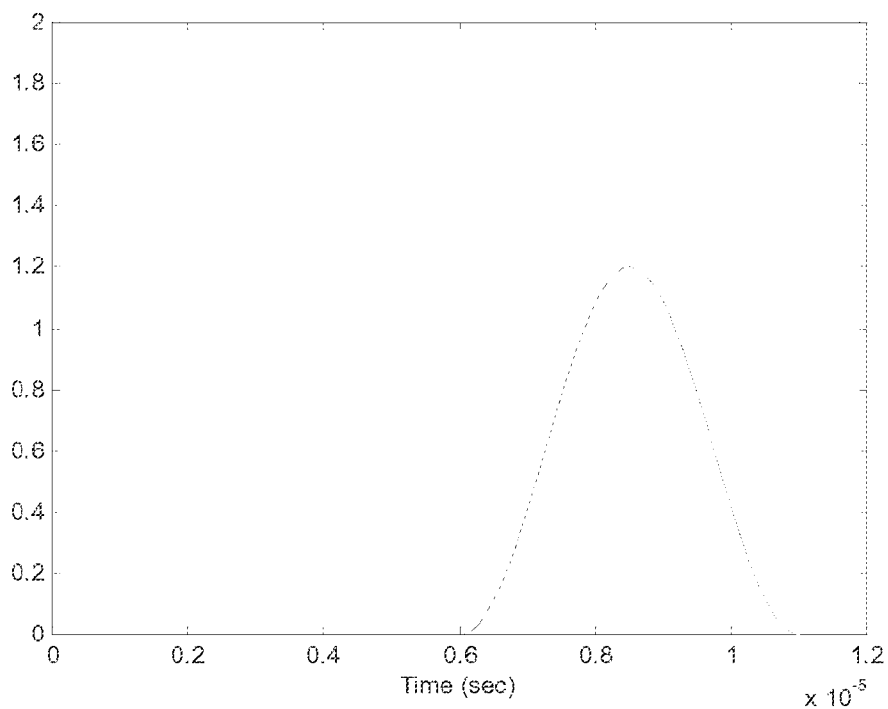
Figure 5A:
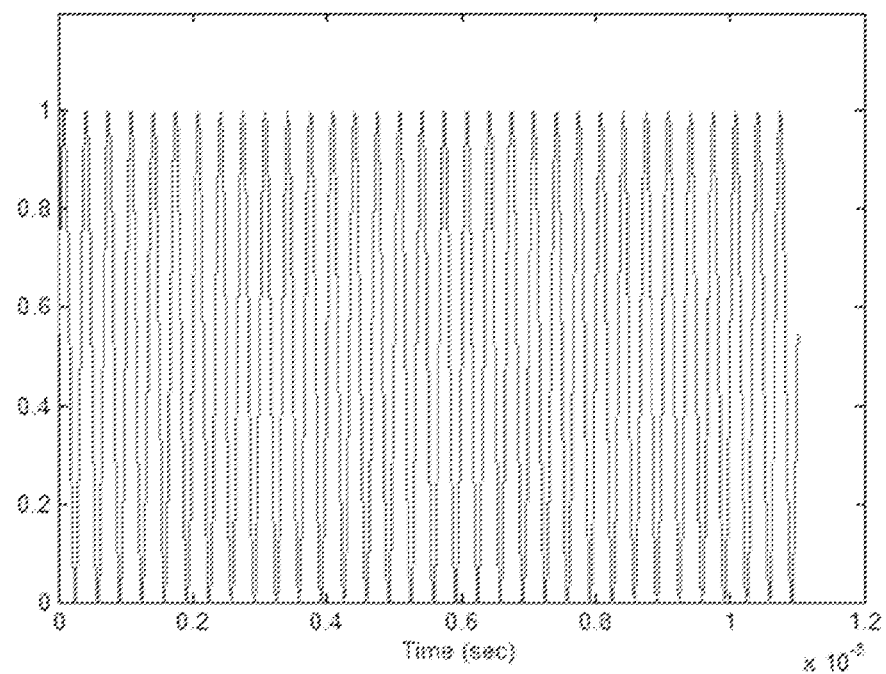
Figure 5B:
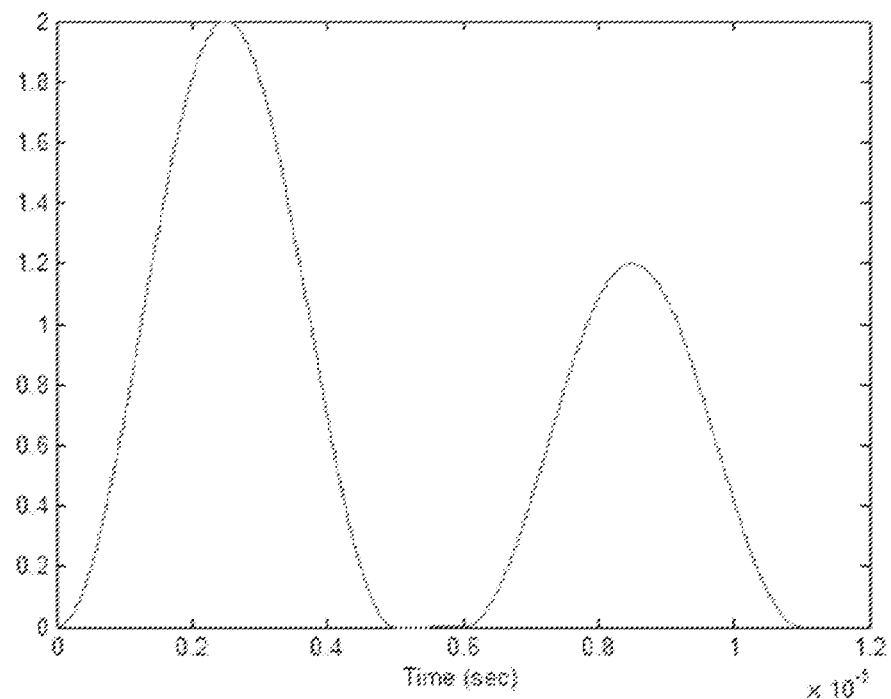
Figure 5C:
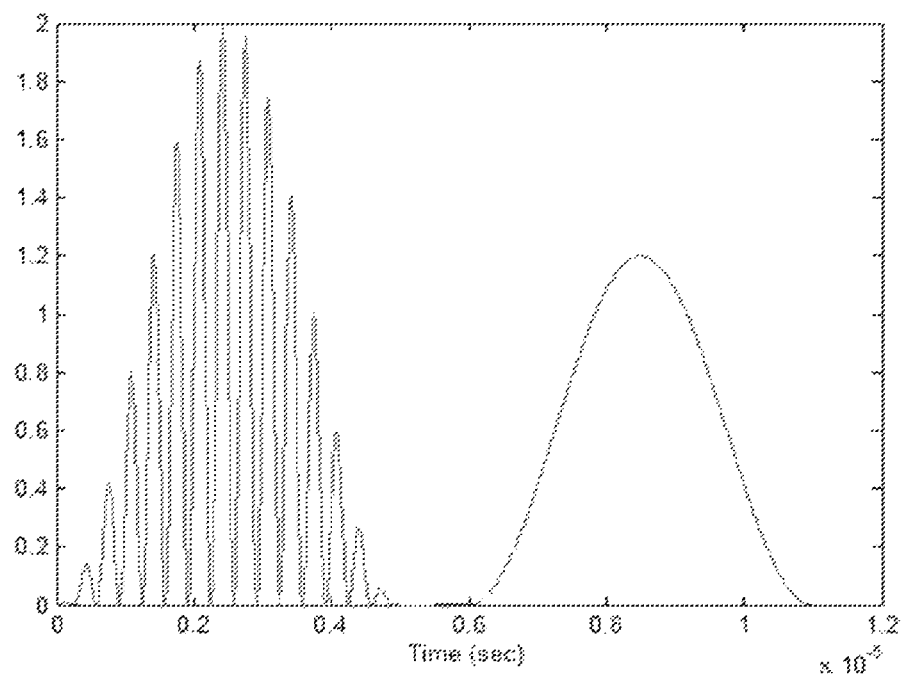
Figure 5D:
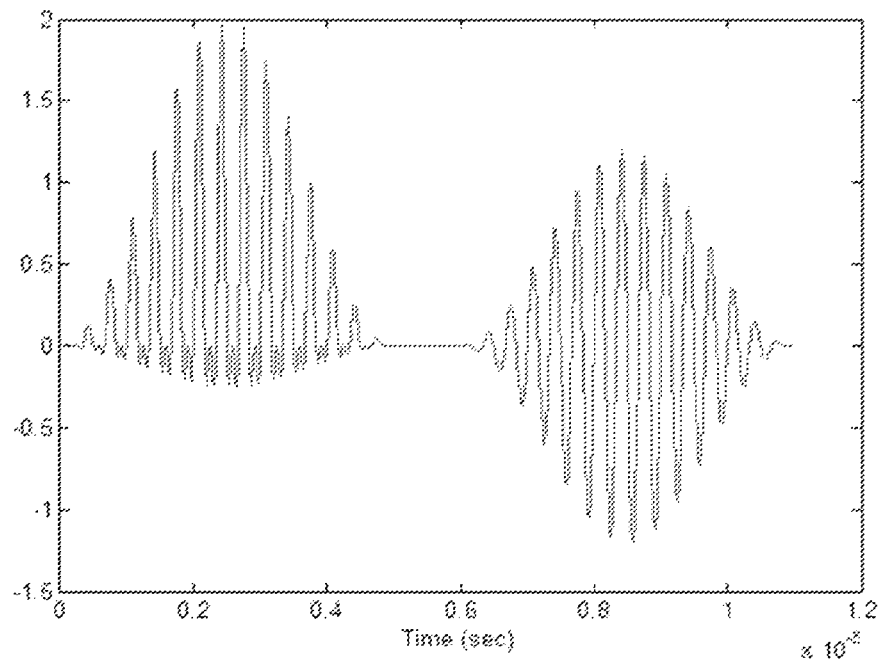
Figure 5E:
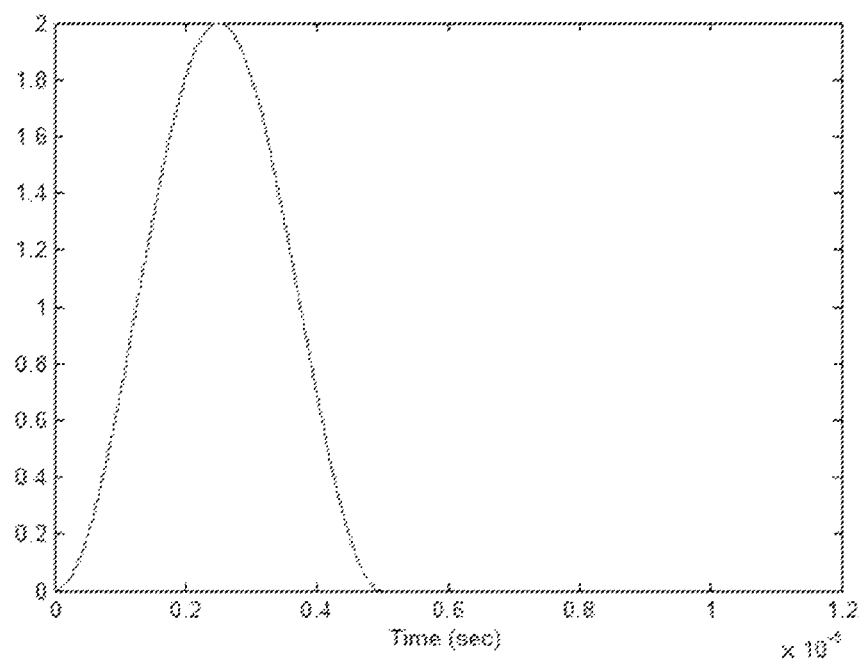
Figure 5F:
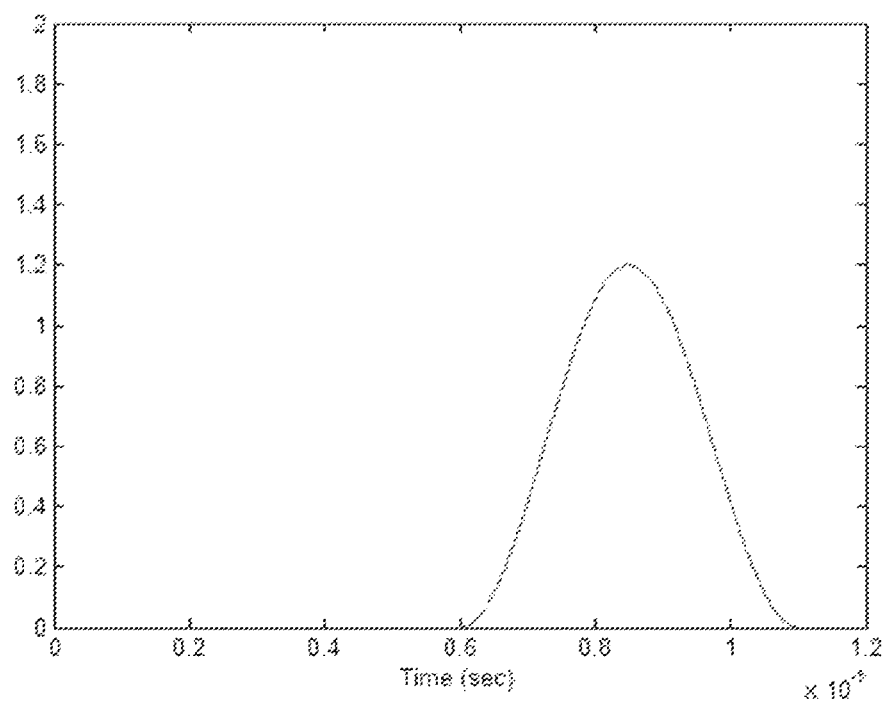
Figure 6A:
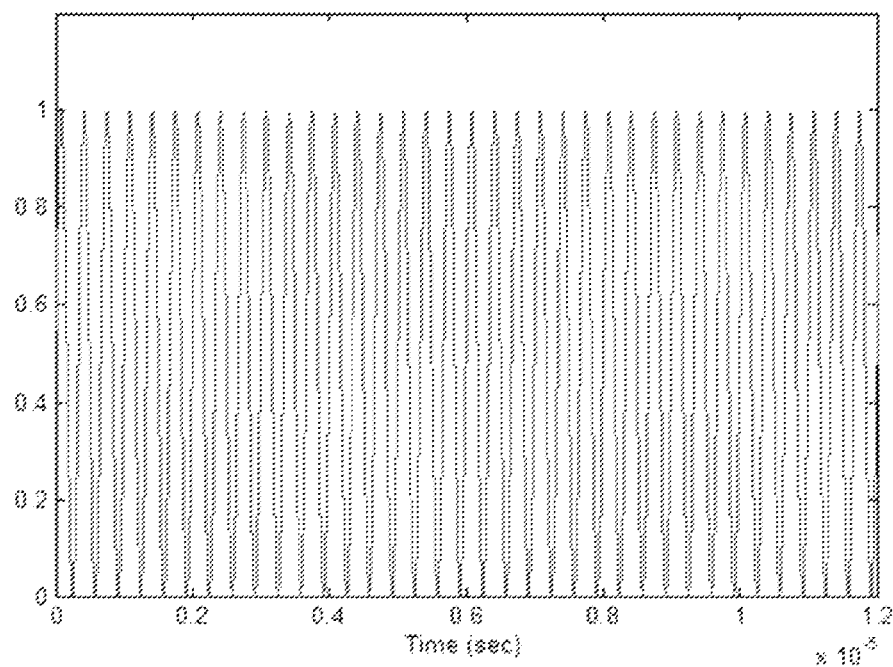
Figure 6B:
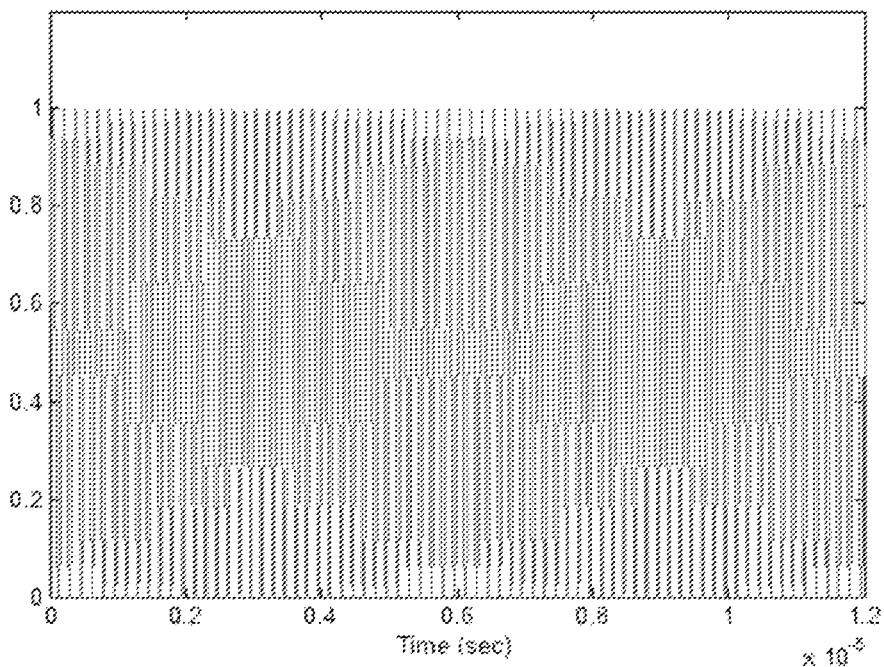
Figure 6C:
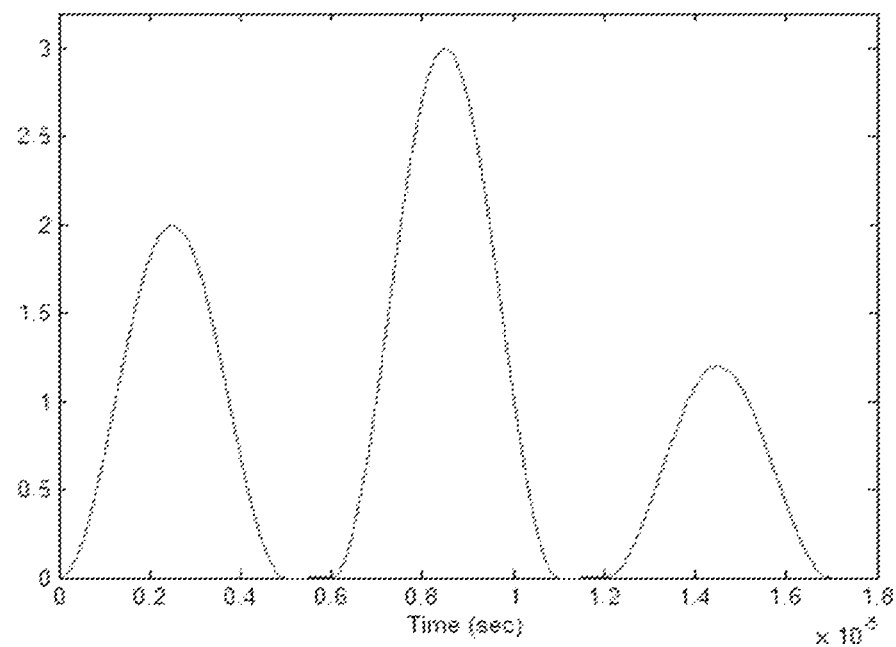
Figure 6D:
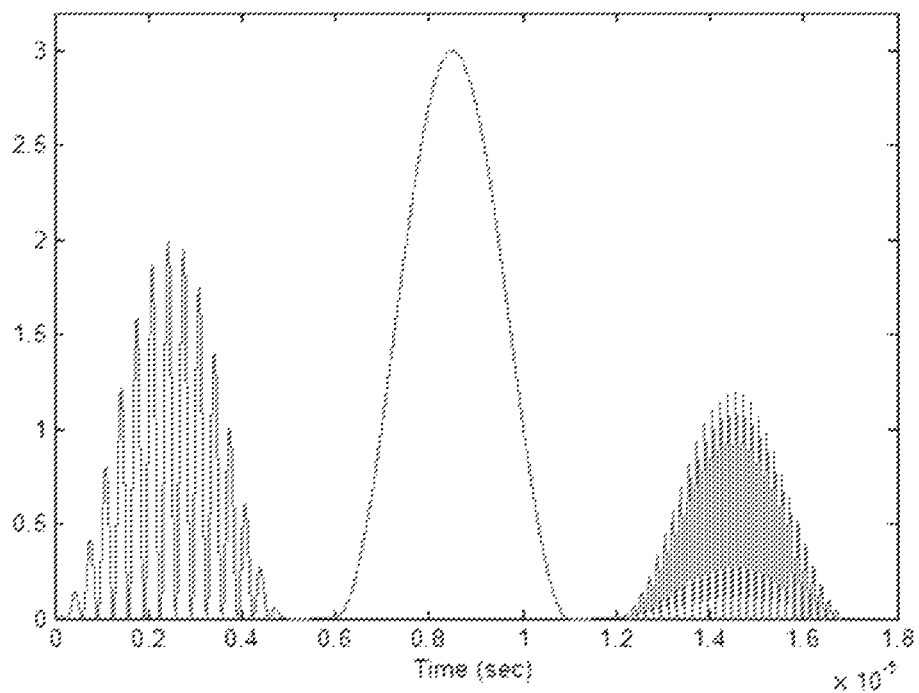
Figure 6E:
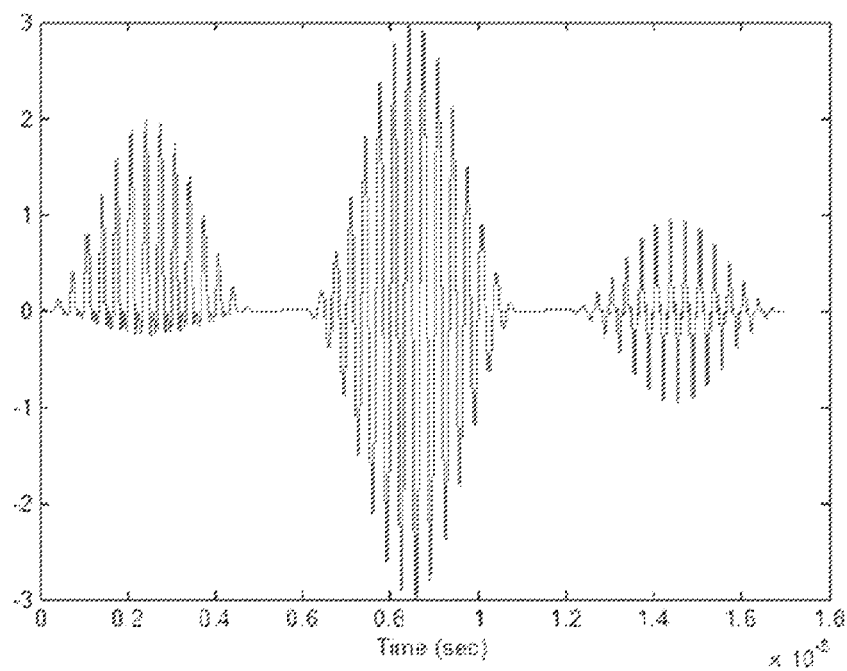
Figure 6F:
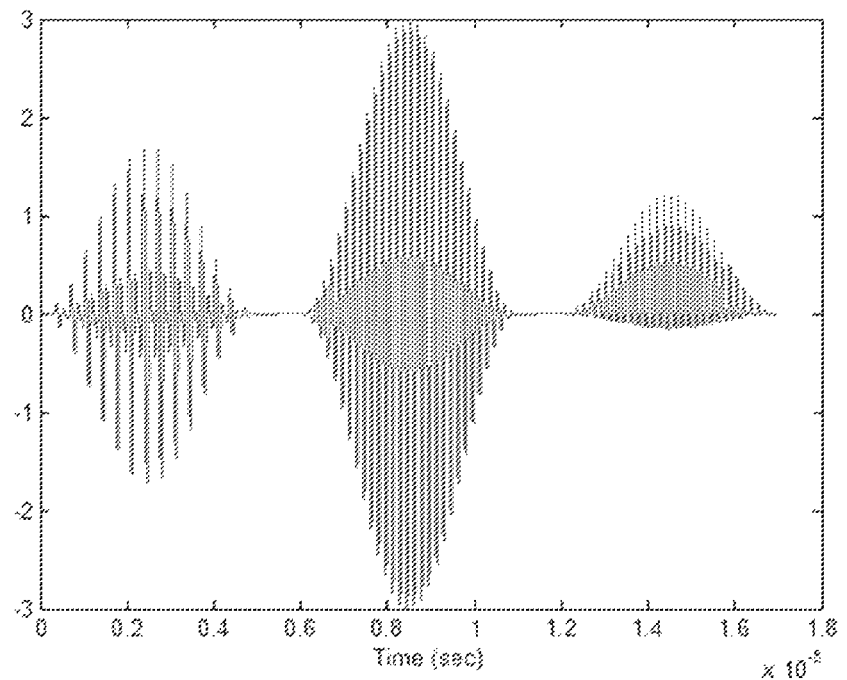
Figure 6H:
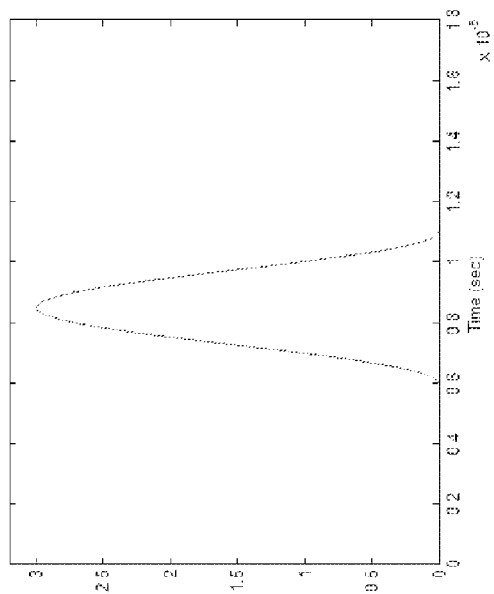
Figure 6G:
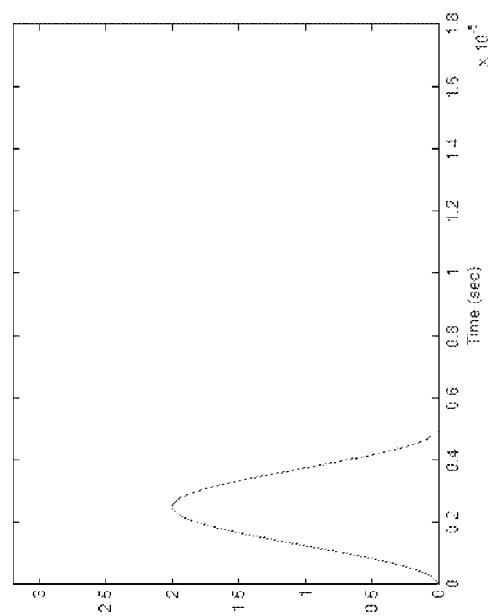
Figure 6I:
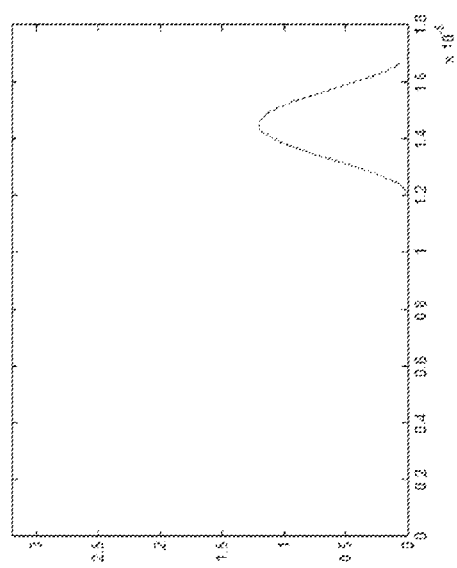
Figure 7A:
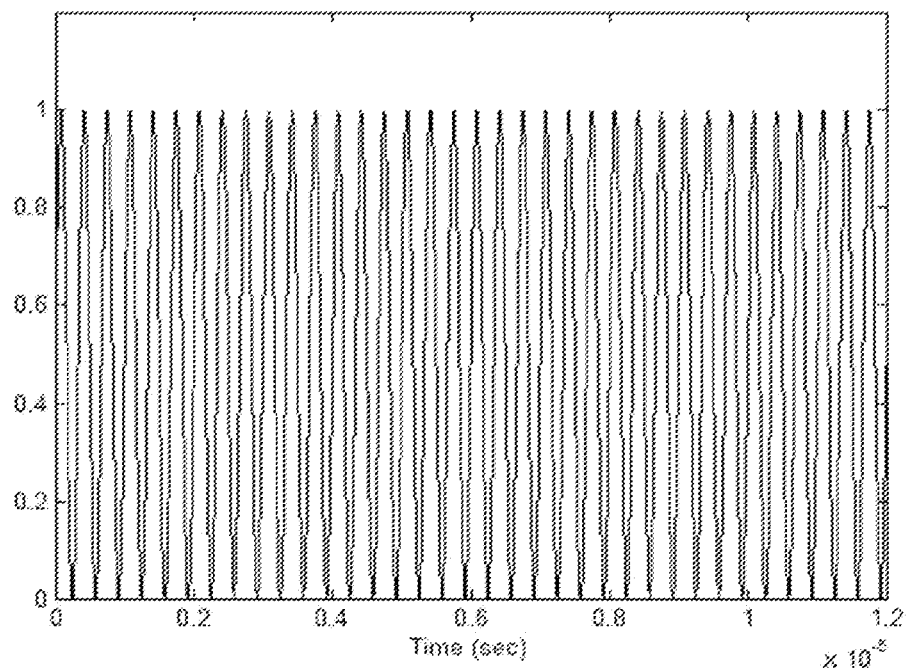
Figure 7B:
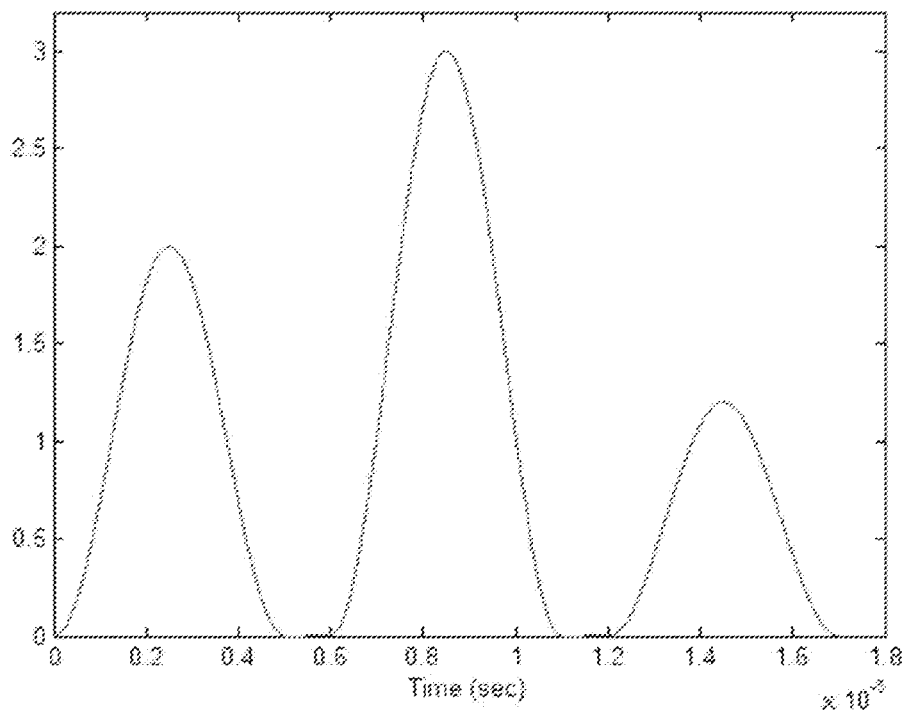
Figure 7C:
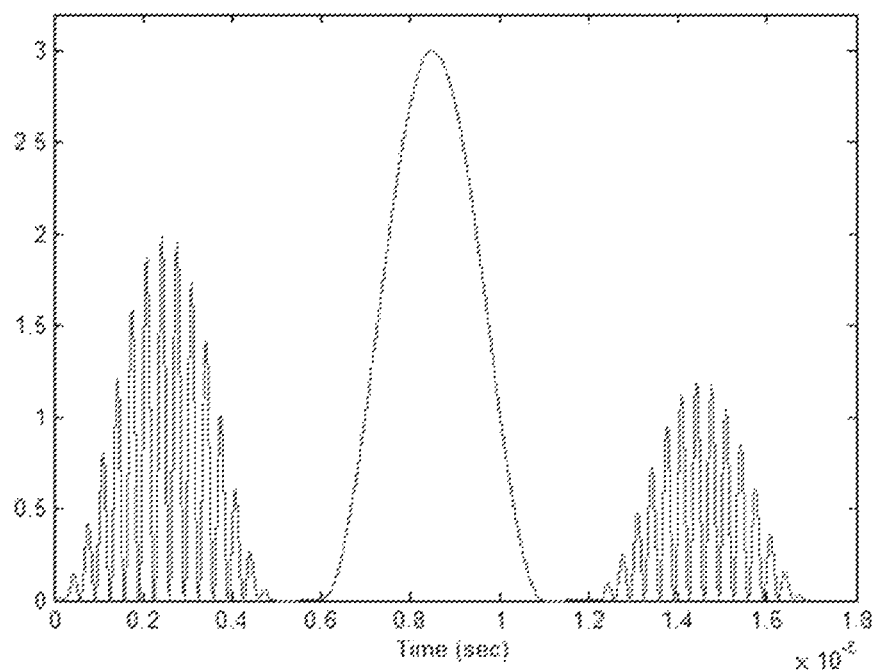
Figure 7D:
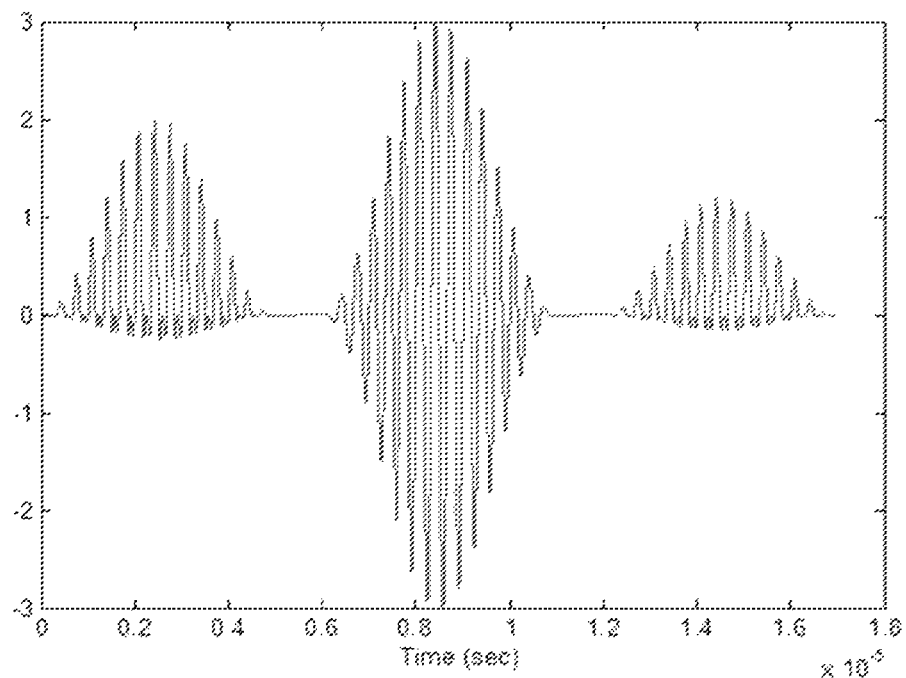
Figure 7E:
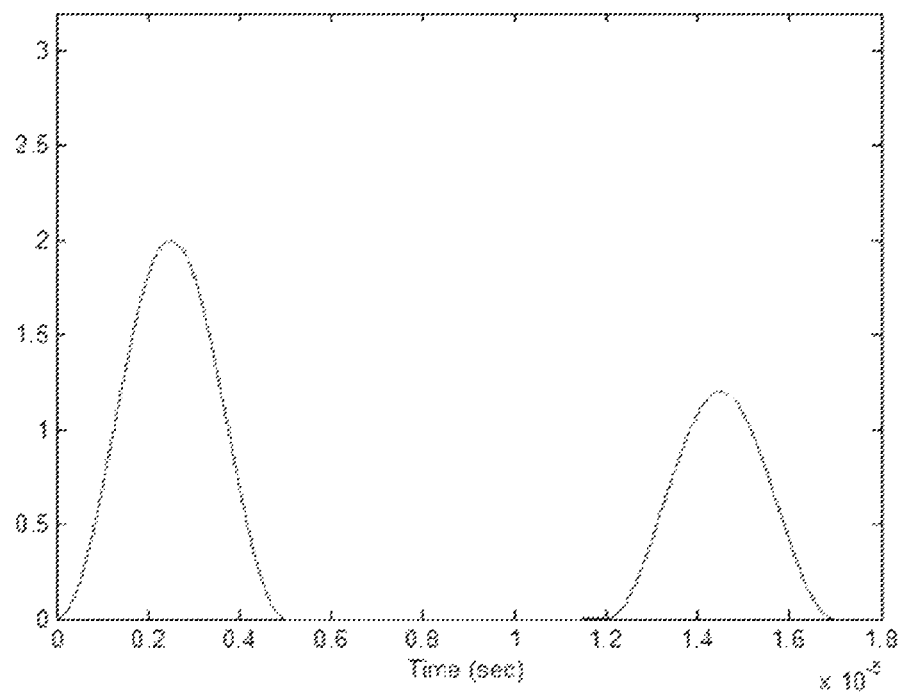
Figure 7F:
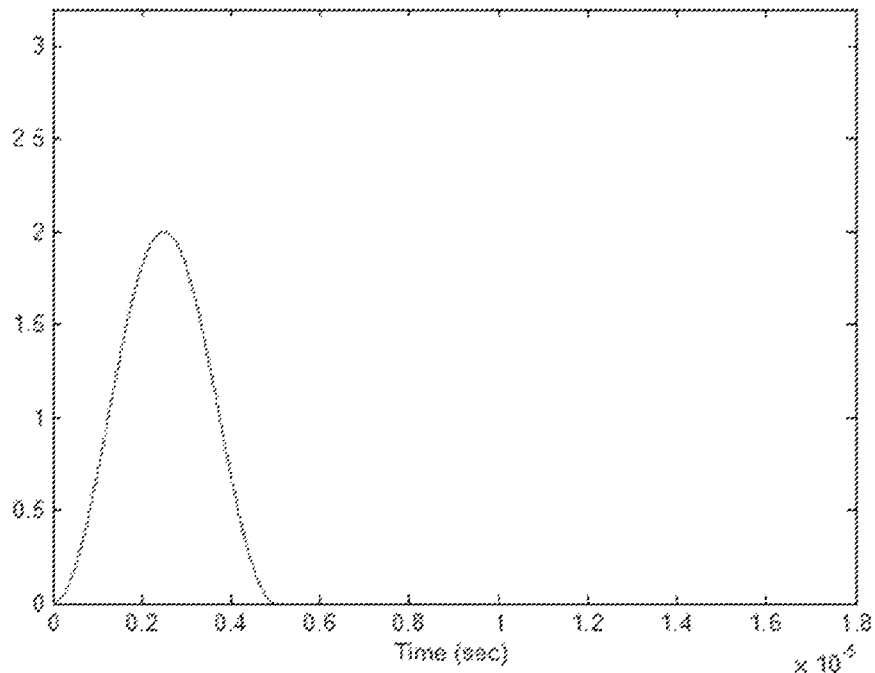
Figure 7G:
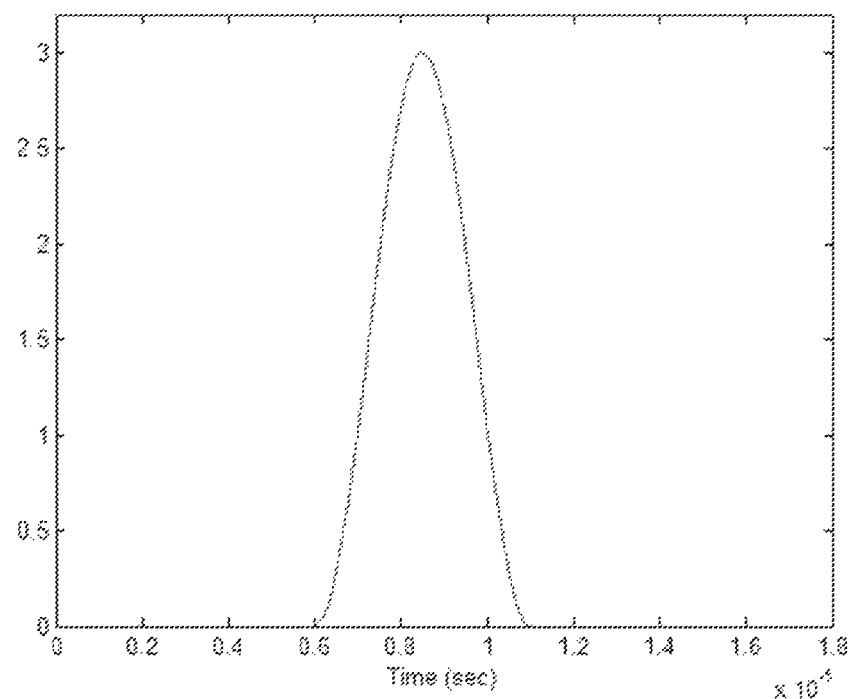
Figure 7H:
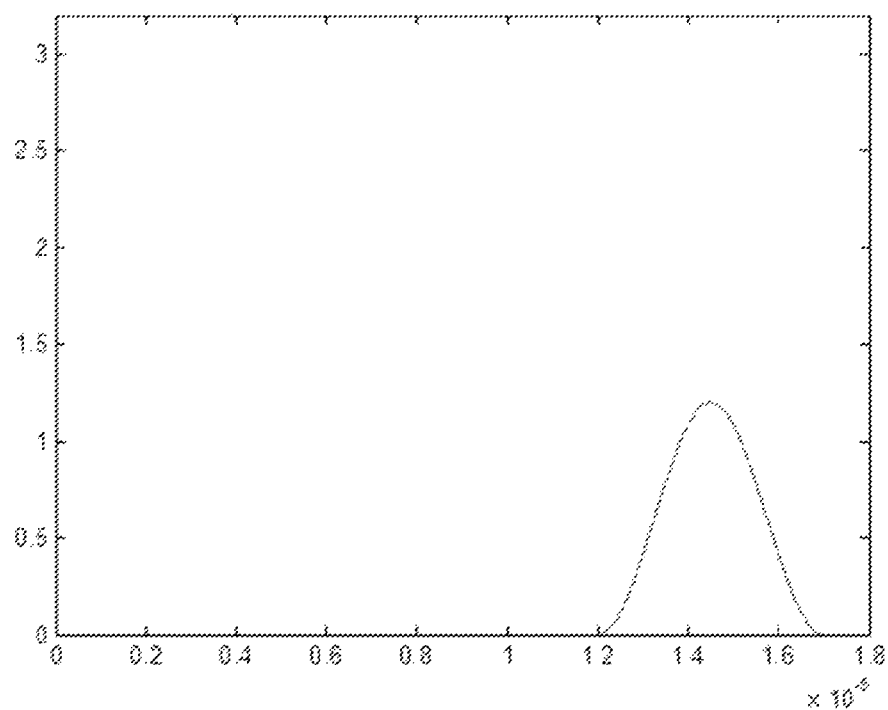

Similarly, using such a "one-component de-modulation method", one could de-modulate Total_Signal to recover the particle induced electronic pulse signal $S_2(t)$. FIG. 4 shows the process of the analog modulation and de-modulation here. FIGS. 4A and 4B show the analog signals used to modulate the $1^{st}$ and $2^{nd}$ light source, respectively. In this example, modulation frequency for the $1^{st}$ and $2^{nd}$ light source is 3 MHz ($f_1$) and 6 MHz ($f_2$), respectively. FIG. 4C shows the total detected electronic pulse signal if no modulation is employed for either light source. A particle/cell passes through the $1^{st}$ OIZ and $2^{nd}$ OIZ sequentially and generate the $1^{st}$ and $2^{nd}$ pulse, respectively. In this example, we assume that particle/cell diameter is 10 microns, passing through the OIZs with a 15 micron along the particle/cell flowing direction, and the linear velocity of the particle/cell is assumed to be 5 m/sec. Furthermore, we assume that the center-to-center distance between these two OIZs is 30 microns. Therefore, the width of the generated individual particle-induced electronic pulse is estimated to be 5 μs (i.e. (10 μm+15 μm)/(5 m/s)) and the separation between two pulse peaks is estimated to be 6 μs (i.e. 30 μm/(5 m/s). FIG. 4D shows the total detected electronic signals when both light sources are modulated using the modulation signals of FIG. 4A and FIG. 4B, respectively. FIGS. 4E and 4F illustrate the intermediate signal when de-modulation is applied to the total signal of FIG. 4D to recover the $1^{st}$ pulse profile and $2^{nd}$ pulse profile, respectively. FIGS. 4G and 4H show the recovered $1^{st}$ and $2^{nd}$ electronic pulse profiles, respectively, generated as the particle passes through the $1^{st}$ and $2^{nd}$ light beams at two OIZs. Note that an amplification/scaling factor of 2 is applied to the signals on FIGS. 4G and 4H after the signals at FIGS. 4E and 4F are filtered by a low-pass filter with a cut-off frequency of 1 MHz.

Quadrature De-Modulation

In a second approach of quadrature demodulation, we consider the phase differences between the modulation signals applied to excitation light beams and the electronic signals from the photodetector. The total electronic signals Total_Signal from a photodetector in equation (1) is as follows:

$$\text{Total}_{signal} = S_1(t)(\sin(2\pi f_1 t + \phi_3)+1) + S_2(t)(\sin(2\pi f_2 t + \phi_4)+1). \quad (4)$$

In order to recover $S_1(t)$, we would multiply Total_Signal with its corresponding modulation signal $\sin(2\pi f_1 t)$ and a 90-degree phase-shift signal $\cos(2\pi f_1 t)$, then we have obtained two Intermediate_Signal_1 and Intermediate_Signal_2

$$\text{Intermediate\_Signal\_1} = \text{Total\_Signal} * \sin(2\pi f_1 t) \quad (5)$$
$$= S_1(t)\sin(2\pi f_1 t + \varphi_3) * \sin(2\pi f_1 t) +$$
$$S_1(t)\sin(2\pi f_1 t) + S_2(t)\sin(2\pi f_2 t + \varphi_4) *$$
$$\sin(2\pi f_1 t) + S_2(t)\sin(2\pi f_1 t)$$
$$= 0.5 S_1(t)\cos(\varphi_3) - 0.5 S_1(t)\cos(4\pi f_1 t + \varphi_3) +$$
$$S_1(t)\sin(2\pi f_1 t) +$$
$$0.5 S_2(t)\cos(2\pi(f_2 t - f_1 t) + \varphi_4) -$$
$$0.5 S_2(t)\cos(2\pi(f_2 t + f_1 t) + \varphi_4) +$$
$$S_2(t)\sin(2\pi f_1 t)$$

-continued $$\begin{aligned}\text{Intermediate\_Signal\_2} &= \text{Total\_Signal} * \cos(2\pi f_1 t) \quad (6)\\
&= S_1(t)\sin(2\pi f_1 t + \varphi_3) * \cos(2\pi f_1 t) +\\
&\quad S_1(t)\cos(2\pi f_1 t) + S_2(t)\sin(2\pi f_2 t + \varphi_4) *\\
&\quad \cos(2\pi f_1 t) + S_2(t)\cos(2\pi f_1 t)\\
&= 0.5S_1(t)\sin(\varphi_3) + 0.5S_1(t)\sin(4\pi f_1 t + \varphi_3) +\\
&\quad S_1(t)\cos(2\pi f_1 t) +\\
&\quad 0.5S_2(t)\sin(2\pi(f_2 t + f_1 t) + \varphi_4) +\\
&\quad 0.5S_2(t)\sin(2\pi(f_2 t - f_1 t) + \varphi_4) +\\
&\quad S_2(t)\cos(2\pi f_1 t)\end{aligned}$$

Thus, the above Intermediate_Signal_1 in equation (5) has multiple components, including a term $S_1(t)\cos(\phi_3)$, and other terms with $S_1(t)$ and $S_2(t)$ being modulated with sine-wave or cosine-wave forms at different frequencies of $f_1$, $2f_1$, $(f_1+f_2)$ or $|f_1-f_2|$. Similarly, Intermediate_Signal_2 in equation (6) has multiple components, including a term $S_1(t)\sin(\phi_3)$, and other terms with $S_1(t)$ and $S_2(t)$ being modulated with sine-wave or cosine-wave forms at different frequencies of $f_1$, $2f_1$, $(f_1+f_2)$ or $|f_1-f_2|$. Similar to Intermediate_Signal in equation (3), by choosing appropriate values of modulation frequencies of $f_1$ and $f_2$ so that the values of $f_1$ and $|f_1-f_2|$ are preferably at least two-times of the frequency bandwidth of the signal $S_1(t)$, Intermediate_Signal_1 in equation (5) and Intermediate_Signal_2 in equation (6) can be processed through a low-pass filter to obtain terms of term $S_1(t)\cos(\phi_3)$ and term $S_1(t)\sin(\phi_3)$, respectively. Thus, signal $S_1(t)$ can be calculated through $$S_1(t) = \sqrt{(S_1(t)\cos(\phi_3))^2 + (S_1(t)\sin(\phi_3))^2} \quad (7)$$

Above procedure in the so-called quadrature de-modulation involves the multiplications of total electronic signals with both modulation signal $\sin(2\pi f_1 t)$ and a 90-degree phase-shift signal $\cos(2\pi f_1 t)$, it is capable of de-modulation of phase-shifted electronic signal components.

Similarly, using such a "quadrature de-modulation method", one could de-modulate Total_Signal in equation (5) to recover the particle induced electronic pulse signal $S_2(t)$.

The single-component de-modulation and quadrature de-modulation methods described above were for the cases of two modulated light beams directed two OIZs in a flow cell. Such methods could be readily extended to three or more modulated light beams focused onto corresponding numbers of OIZs in a flow cell.

Furthermore, whilst above description of single-component de-modulation and quadrature de-modulation was based on modulation of light beams using a sine-wave, these de-modulation methods are also applicable to other waveform based modulations. According to Fourier transform principle, all periodic waveforms could be decomposed into the summation of multiple sine-wave forms having DC component (constant component), $1^{st}$ harmonics, $2^{nd}$ harmonics, $3^{rd}$ harmonics etc. Thus, total signal in above equation (2) and (4) would include more sine-wave terms at all these harmonic frequencies, when the light source is modulated with waveforms other than sine-waves. During de-modulation processes, similar multiplication step (as shown in equations (3), (5) and (6)) would be taken where total signal in equation (2) and (4) is multiplied by sine or cosine functions at $1^{st}$ harmonic frequency (assuming that the $1^{st}$ harmonic component magnitude is to be recovered since for many periodic waveforms, $1^{st}$ harmonic would have the largest amplitude among all harmonics). Using similar low-pass filter, one can recover the electronic pulse profile caused by particle/cell passing through an optical interrogation zone. It is worthwhile to describe that the selection of appropriate modulation frequencies is especially important when modulation signals are taken non-sine waveforms, in order to effectively recover signals through low-pass filtering of the intermediate signals during de-modulation process. As described above for intermediate signals of equations (3), (5) and (6) when modulation signals are of sine waveforms, the modulation frequencies of $f_1$ and $f_2$ should be chosen properly so that the values of $f_1$ and $(f_1-f_2)$ are preferably at least two-times of the frequency bandwidth of the signal $S_1(t)$. When a non-sine waveform is used for modulation, for example, a square waveform or a digital modulation may be applied to modulate light sources due to the possibility of higher-frequency modulation. Assume that two modulation waveforms have the first harmonic frequencies of $f_{h1}$ and $f_{h2}$. The intermediate signals after multiplying the total detected signals with the modulation $1^{st}$ harmonic signals would result in a signal term and other signals terms being modulated with sine-wave or cosine-wave forms at different frequencies of $f_{h1}$, $2f_{h1}$, ... $nf_{h1}$, ..., and $(f_{h1}+f_{h2})$, $(f_{h1}+2f_{h2})$, ... $(f_{h1}+nf_{h2})$, ... and $|f_{h1}-f_{h2}|$, ... $|f_{h1}-nf_{h2}|$, ... etc. Thus when two light sources are modulated at two different frequencies (harmonics being $f_{h1}$ and $f_{h2}$), the modulation frequencies of $f_{h1}$ and $f_{h2}$ should be chosen properly values of $f_1$ and $|f_{h1}-f_{h2}|$, $|f_{h1}-2f_{h2}|$, ... $|f_{h1}-nf_{h2}|$, ..., are all preferably at least two-times of the frequency bandwidth of the signal $S_1(t)$. This is an important requirement for effective recovery and filtering of the signal $S_1(t)$ using the de-modulation methods described above.

In the present invention, light beams from different light sources are focused onto or directed to different optical interrogation zones (OIZs). Thus, for above examples, electronic signal component $S_1(t)$ and $S_2(t)$ would occupy different time windows, as long as there are sufficient distances between two OIZs and as long as the gap between two OIZs is large than particle diameter. Such a spatial separation between different OIZs and time-domain separation between signal components $S_1(t)$ and $S_2(t)$ are preferred, and have special advantages and benefits compared with the condition where light beams from different OIZs are overlapping or coincide with each other. Firstly, if two (or more) light beams from different light sources are directed to the same OIZ, different fluorescent molecules that can be excited by different wavelengths would be excited simultaneously as particle/cell passes through the OIZ. If their fluorescent emission spectra overlap, then fluorescent signals from different fluorescent molecules would be detected by the same photodetector. Thus, the dynamic range of the photodetector would be shared by the measurements on two or more fluorescent molecules. As a result, each fluorescent molecule may occupy only partial ranges of the complete dynamic range. On the other hand, for the present invention, light beams from different light sources are focused onto or directed to different optical interrogation zones (OIZs). Thus, no two fluorescent molecules would be excited simultaneously if they are excitable by two different light wavelengths. In another word, even if these two or more fluorescent molecules emit the same emission spectra range and are detected by the same photodetector, each type of fluorescent molecule is still able to utilize entire dynamic range of the photodetector. Secondly, when light beams from different light sources coincide and are directed onto the same OIZ, even if these light beams are modulated at different frequencies, signals for different fluorescent molecules may interfere with each other. As a result, there will be cross-talks between electronic signals corresponding to different fluorescent molecules, even if these fluorescent molecules are excited by different light sources. Consider the following example where light beam from $1^{st}$ light source at one light wavelength is modulated at frequency $f_1$ and light beam from $2^{nd}$ light source at a different wavelength is modulated at frequency $f_2$ and both light beams are directed to the same optical interrogation zone (OIZ). When a particle containing one type of fluorescent molecule to be excited by the $1^{st}$ light source passes through the OIZ, theoretically there should be only electronic signals at frequency $f_1$, corresponding to excitation of this type of fluorescent molecules in the particle/cell. In practice, due to the noises in the $1^{st}$ light source, in the photodetector and in associated electronic circuits, there will be noise components occurring at frequency $f_2$, which will be detected as "signal from some other fluorescent molecules being excited by the $2^{nd}$ light source". Importantly, such noise-signal amplitudes at frequency $f_2$ may increase with the real signal amplitude associated with the fluorescent molecules in the particle/cell, due to noise natures in the photodetector and associated circuits. For example, it is well-known that a photodetector would have larger noises in amplitudes when it is exposed to a larger-intensity light signal. On the other hand, when light beams from different light sources are directed to different optical interrogation zones (OIZs), there will be no such direct interference of signals for different fluorescent molecules excited by different light beams with different wavelengths at different locations. Electronic signals having modulation frequency $f_1$ would be detected from photodetectors only for the time window when the particle travels through OIZ1 and will not be detected for other time ranges when the particle travels outside OIZ1. Similarly, electronic signals having modulation frequency $f_2$ would be detected from photodetectors only for the time window when particle travels through OIZ2 and will not be detected for other time ranges when the particle is outside OIZ2. For the particle that contains only fluorescent molecules being excited by the $1^{st}$ light beam in OIZ1, there will be no signal associated with $2^{nd}$ light excitation source when it travels through OIZ1, even though the noises would be larger during such a time window since particle's fluorescent molecules are excited by the $1^{st}$ light beam and would emit lights to be detected at the photodetector. When this particle moves through OIZ2, there would be minimum or no signal at all corresponding to the $2^{nd}$ light beam since it does not contain fluorescent molecules being excited by the $2^{nd}$ light source. The minimum signal, if any, at such time window, is simply associated with dark current of photodetector and other background noises of the circuits and other system components.

EXAMPLE 2

One Intensity-Modulated Light Source and One Non-Modulated Light Source

In above sections, both light beams are modulated and single-component de-modulation and quadrature demodulation methods are used to recover corresponding electronic pulse profiles from the modulated signals. In following examples, we consider the cases where one light beam is not modulated and modulation is applied to the other light beams. We perform exemplary analysis for the case of two excitation sources where light beam directed to OIZ1 is modulated by a sine-wave signal at a frequency $f_1$ and phase value zero (Mod1=$\sin(2\pi f_1 t)+1$) and light beam directed to OIZ2 is not modulated. Total electronic signals Total_Signal from a photodetector is the sum of the signal associated with emitted light from OIZ1 (Sig1) and OIZ2 (Sig2), respectively, and can be expressed as, $$\text{Total\_Signal} = \text{Sig1} + \text{Sig2} = S_1(t)(\sin(2\pi f_1 t + \phi_3) + 1) + S_2(t) \quad (8)$$

where $S_1(t)$ and $S_2(t)$ are output electronic signal from the photodetector due to particles/cells passing through the $1^{st}$ OIZ and the $2^{nd}$ OIZ, respectively, when no modulation is applied to either one of the light sources. An electronic processor is used to de-modulate the Total_Signal to recover electronic signal $S_1(t)$ and $S_2(t)$ so that the light intensity (i.e. fluorescence or side-scatter) can be derived at the corresponding detection channel. Similar to the example of two modulated light sources, both single-component de-modulation method and quadrature de-modulation method can be used here to recover electronic signals signal $S_1(t)$ and $S_2(t)$.

Single-Component De-Modulation

For single component de-modulation, we would multiply Total_Signal with its corresponding modulation signal $\sin(2\pi f_1 t)$, then we have $$\begin{aligned}\text{Intermediate\_Signal} &= \text{Toatl\_Signal} * \sin(2\pi f_1 t) \quad (9)\\ &= S_1(t)\sin(2\pi f_1 t + \varphi_3) * \sin(2\pi f_1 t) +\\ &\quad S_1(t)\sin(2\pi f_1 t) + S_2(t)\sin(2\pi f_1 t)\\ &= 0.5 S_1(t)\cos\varphi_3 - 0.5 S_1(t)\cos(4\pi f_1 t + \varphi_3) +\\ &\quad S_1(t)\sin(2\pi f_1 t) + S_2(t)\sin(2\pi f_1 t)\end{aligned}$$

Thus, the above Intermediate_Signal has multiple components, including a term $S_1(t)$, and other terms with $S_1(t)$ and $S_2(t)$ being modulated with sine-wave or cosine-wave forms at different frequencies of $f_1$, or $2f_1$. Similar to the analysis described above for equation (3), the modulation frequency $f_1$ should be chosen to be at least two times of signal bandwidth. For example, the signal bandwidth may be about 1 MHz and $f_1$ could have a value of 3 MHz. Using a low pass filter with a cut-frequency of, e.g. 1 MHz, particle-induced electronic pulse signal $S_1(t)$ could be recovered by filtering the Intermediate_Signal. Therefore, except the $1^{st}$ term, all the other terms in equation (9) would be filtered out by the low-pass filter, thus recover signal $S_1(t)\cos\phi_3$ from the Intermediate_Signal. Note that phase angle $\phi_3$ reflects the phase difference of the electronic signal component at modulation frequency $f_1$ from the photodetector, relative to the phase of modulation signal itself (phased at zero as reference). As described above, the factors contributing to such a phase change (or phase difference) include the response-time-delay of light source between the modulation electronic signal and the modulated light beam at the corresponding OIZ, the response time or relaxation time or life time of fluorescent molecules, and the response time of photodetectors, and other possible time delays within the system from modulation of light sources to detecting fluorescent signals on the photodetectors. U.S. Pat. Nos. 5,196,709 and 5,270,548 described the method and apparatus capable of measuring the life time of fluorescent molecules; the disclosure of which is herein incorporated by reference.

In this approach of "one-component de-modulation", we do not take into account the phase differences between the modulation signals applied to excitation light beams and the electronic signals from the photodetector. In another word, it is assumed that there is no phase change or phase difference for the electronic signals from the photodetector, relative to the phase values of the modulation signals. Under such a consideration, phase angle $\phi_3$ can be approximated as zero, Thus, particle induced electronic pulse signal $S_1(t)$ is recovered ($S_1(t)\cos \phi_3 = S_1(t)$).

Furthermore, particle-induced electronic pulse signal $S_2(t)$ could also be recovered by filtering Total_Signal in equation (8) with such a low pass filter. Therefore, except the $1^{st}$ term, all the other terms in equation (8) would be filtered out by the low-pass filter, thus recover signal $S_2(t)$ from the Total_Signal.

FIG. 5 shows the process of the analog modulation and de-modulation described in this example. FIG. 5A shows an analog signal used to modulate the $1^{st}$ light source. In this example, the modulation frequency for the $1^{st}$ light source is 3 MHz ($f_1$). FIG. 5B shows the total detected electronic pulse signal if no modulation is employed for the $1^{st}$ light source. A particle/cell passes through the $1^{st}$ OIZ and $2^{nd}$ OIZ sequentially and generate the $1^{st}$ and $2^{nd}$ pulse, respectively. In this example, we assume that particle/cell diameter is 10 microns, passing through the OIZs with a 15 micron along the particle/cell flowing direction, and the linear velocity of the particle/cell is assumed to be 5 m/sec. Furthermore, we assume that the center-to-center distance between these two OIZs is 30 microns. Therefore, the width of the generated individual particle-induced electronic pulse is estimated to be 5 µs (i.e. (10 µm+15 µm)/(5 m/s)) and the separation between two pulse peaks is estimated to be 6 µs (i.e. 30 µm/(5 m/s). FIG. 5C shows the total detected electronic signals when the $1^{st}$ light source is modulated using the modulation signal of FIG. 5A. FIG. 5D illustrates the intermediate signal when de-modulation is applied to the total signal of FIG. 5C to recover the $1^{st}$ pulse profile. FIGS. 5E and 5F show the recovered $1^{st}$ and $2^{nd}$ electronic pulse profiles, respectively, generated as the particle passes through the $1^{st}$ and $2^{nd}$ light beams at two OIZs. Note that an amplification/scaling factor of 2 is applied to the signals on FIG. 5E after the signal at FIG. 5D is filtered with a low-pass filter with a cut-off frequency of 1 MHz.

Quadrature De-Modulation

For quadrature demodulation, we consider the phase differences between the modulation signals applied to excitation light beams and the electronic signals from the photodetector. In order to recover $S_1(t)$ from equation (8), we would multiply Total_Signal in equation (8) with its corresponding modulation signal $\sin(2\pi f_1 t)$ and a 90-degree phase-shift signal $\cos(2\pi f_1 t)$, then we have obtained two Intermediate_Signal_1 and Intermediate_Signal_2

$$\begin{aligned}
\text{Intermediate\_Signal\_1} &= \text{Toatl\_Signal} * \sin(2\pi f_1 t) \quad (10)\\
&= S_1(t)\sin(2\pi f_1 t + \varphi_3) * \sin(2\pi f_1 t) +\\
&\quad S_1(t)\sin(2\pi f_1 t) + S_2(t)\sin(2\pi f_1 t)\\
&= 0.5S_1(t)\cos\varphi_3 - 0.5S_1(t)\cos(4\pi f_1 t + \varphi_3) +\\
&\quad S_1(t)\sin(2\pi f_1 t) + S_2(t)\sin(2\pi f_1 t)
\end{aligned}$$

$$\begin{aligned}
\text{Intermediate\_Signal\_2} &= \text{Toatl\_Signal} * \cos(2\pi f_1 t) \quad (11)\\
&= S_1(t)\sin(2\pi f_1 t + \varphi_3) * \cos(2\pi f_1 t) +\\
&\quad S_1(t)\cos(2\pi f_1 t) + S_2(t)\cos(2\pi f_1 t)\\
&= 0.5S_1(t)\sin\varphi_3 + 0.5S_1(t)\sin(4\pi f_1 t + \varphi_3) +\\
&\quad S_1(t)\cos(2\pi f_1 t) + S_2(t)\cos(2\pi f_1 t)
\end{aligned}$$

Thus, the above Intermediate_Signal_1 in equation (10) has multiple components, including a term $S_1(t)\cos(\phi_3)$, and other terms with $S_1(t)$ and $S_2(t)$ being modulated with sine-wave or cosine-wave forms at different frequencies of $f_1$ or $2f_1$. Similarly, Intermediate_Signal_2 in equation (11) has multiple components, including a term $S_1(t)\sin(\phi_3)$, and other terms with $S_1(t)$ and $S_2(t)$ being modulated with sine-wave or cosine-wave forms at different frequencies of $f_1$ or $2f_1$. Similar to the analysis described above for equation (3), the modulation frequency $f_1$ should be chosen to be at least two times of signal bandwidth. Thus, Intermediate_Signal_1 in equation (10) and Intermediate_Signal_2 in equation (11) can be processed through a low-pass filter to obtain terms of term $S_1(t)\cos(\phi_3)$ and term $S_1(t)\sin(\phi_3)$, respectively. Thus, signal $S_1(t)$ can be calculated through $$S_1(t) = \sqrt{(S_1(t)\cos(\phi_3))^2 + (S_1(t)\sin(\phi_3))^2} \quad (12)$$

The single-component de-modulation and quadrature de-modulation methods described above were for the cases of one modulated light beam and one non-modulated light beam directed two OIZs in a flow cell. Such methods could be readily extended to three or more light beams focused onto corresponding numbers of OIZs in a flow cell, with at least one modulated beam and one non-modulated beam.

Furthermore, whilst above description of single-component de-modulation and quadrature de-modulation was based on modulation of light beams using a sine-wave, these de-modulation methods are also applicable to other waveform based modulations. According to Fourier transform principle, all periodic waveforms could be decomposed into the $1^{st}$ summation of multiple sine-wave forms having DC component (constant component), harmonics, $2^{nd}$ harmonics, $3^{rd}$ harmonics etc. Thus, total signal in above equation (8) would include more sine-wave terms at all these harmonic frequencies, when the light source is modulated with waveforms other than sine-waves. During de-modulation processes, similar multiplication step (as shown in equations (9), (10) and (11)) would be taken where total signal in equation (8) is multiplied by sine or cosine functions at $1^{st}$ harmonic frequency (assuming that the $1^{st}$ harmonic component magnitude is to be recovered since for many periodic waveforms, $1^{st}$ harmonic would have the largest amplitude among all harmonics). Using similar low-pass filter, one can recover the electronic pulse profile caused by particle/cell passing through an optical interrogation zone. It is interesting to discuss how appropriate modulation frequency should be chosen when modulation signals are taken non-sine waveforms, in order to effectively recover signals through low-pass filtering of the intermediate signals during demodulation process. As described above for intermediate signals of equations (9), (10) and (11) when modulation signals are of sine waveforms, the modulation frequencies of $f_1$ should be chosen properly so that the value of $f_1$ is preferably at least two-times of the frequency bandwidth of the signal $S_1(t)$. When a non-sine waveform is used for modulation, for example, a square waveform or a digital modulation may be applied to modulate light sources due to the possibility of higher-frequency modulation. Assume that the modulation waveform has the first harmonic frequencies of $f_{h1}$. The intermediate signals after multiplying the total detected signals with the modulation $1^{st}$ harmonic signals would result in a signal term and other signals terms being modulated with sine-wave or cosine-wave forms at different frequencies of $f_{h1}$, $2f_{h1}$, $3f_{h1}$, ... $nf_{h1}$, etc. Thus, if only one light source is modulated or if multiple modulated light sources are modulated with the same modulation signal (thus the same frequency), the modulation frequencies of $f_{h1}$ should be chosen properly, so that $f_{h1}$ is preferably at least two-times of the frequency bandwidth of the signal $S_1(t)$.

In the present invention, light beams from different light sources are focused onto or directed to different optical interrogation zones (OIZs). Thus, for above examples, electronic signal component $S_1(t)$ and $S_2(t)$ would occupy different time windows, as long as there are sufficient distances between two OIZs and as long as the gap between two OIZs is large than particle diameter. Such a spatial separation between different OIZs and time-domain separation between signal components $S_1(t)$ and $S_2(t)$ are preferred, and have special advantages and benefits compared with the condition where light beams from different OIZs are overlapping or coincide with each other. Firstly, if two (or more) light beams from different light sources are directed to the same OIZ, different fluorescent molecules that can be excited by different wavelengths would be excited simultaneously as particle/cell passes through the OIZ. If their fluorescent emission spectra overlap, then fluorescent signals from different fluorescent molecules would be detected by the same photodetector. Thus, the dynamic range of the photodetector would be shared by the measurements on two or more fluorescent molecules. As a result, each fluorescent molecule may occupy only partial ranges of the complete dynamic range. On the other hand, for the present invention, light beams from different light sources are focused onto or directed to different optical interrogation zones (OIZs). Thus, no two fluorescent molecules would be excited simultaneously if they are excitable by two different light wavelengths. In another word, even if these two or more fluorescent molecules emit the same emission spectra range and are detected by the same photodetector, each type of fluorescent molecule is still able to utilize entire dynamic range of the photodetector. Secondly, when light beams from different light sources coincide and are directed onto the same OIZ, even if one light beam is modulated and one light is not modulated, signals for different fluorescent molecules (supposedly due to different light sources at different wavelengths) may interfere with each other. Thus, there will be cross-talks between electronic signals corresponding to different fluorescent molecules. Consider the following example where one light beam from $1^{st}$ light source at one light wavelength is not modulated and another light beam from $2^{nd}$ light source at a different wavelength is modulated at frequency $f_2$ and both light beams are directed to the same optical interrogation zone (OIZ). When a particle containing one type of fluorescent molecule to be excited by the $1^{st}$ light source passes through the OIZ, theoretically there should be only electronic signals corresponding to excitation of this type of fluorescent molecules in the particle/cell. In practice, due to the noises in the $1^{st}$ light source, in the photodetector and in associated electronic circuits, there will be electronic noises occurring at frequency $f_2$, which will be detected as "signal from other fluorescent molecules being excited by the $2^{nd}$ light source". Importantly, such noise-signal amplitudes at frequency $f_2$ may increase with the real electronic signals corresponding to the excitation of the fluorescent molecules in the particle, due to noise natures in the photodetector and associated circuits. For example, it is well-known that a photodetector would have larger noises in amplitudes when it is exposed to a larger-intensity light signal. On the other hand, when light beams from different light sources are directed to different optical interrogation zones (OIZs), there will be no such direct interference of signals for different fluorescent molecules excited by different light beams with different wavelengths at different locations. Un-modulated electronic signals would be detected from photodetectors only for the time window when the particle travels through OIZ1 and will not be detected for other time ranges when the particle travels outside OIZ1. Similarly, electronic signals having modulation frequency $f_2$ would be detected from photodetectors only for the time window when particle travels through OIZ2 and will not be detected for other time ranges when the particle is outside OIZ2. For the particle that contains only fluorescent molecules being excited by the $1^{st}$ light beam in OIZ1, there will be no signal associated with $2^{nd}$ light excitation source when it travels through OIZ1, even though the noises would be larger during such a time window since particle's fluorescent molecules are excited by the $1^{st}$ light beam and emit lights onto the photodetector. When this particle moves through OIZ2, there would be minimum or no signal at all corresponding to the $2^{nd}$ light beam since it does not contain fluorescent molecules being excited by the $2^{nd}$ light source. The minimum signal, if any, at such time window, is simply associated with dark current of photodetector and other background noises of the circuits and other system components.

EXAMPLE 3

Two Intensity-Modulated Light Sources at Same Modulation Frequency and Different Modulation Phases In above examples, modulation applied to different light sources has been based on differences in modulation frequency ($f_1$ and $f_2$ in equation (1)) and in amplitude (1 for modulation $S_1(t)$ and 0 for $S_2(t)$ in equation (8)). Modulation of different light sources could also be based on phase angles of the modulation signals but with the same modulation frequency. Light beam directed to OIZ1 is modulated by a sine-wave signal at a frequency $f_1$ with phase angle 0 (i.e. $Mod1=\sin(2\pi f_1 t)+1$) and light beam directed to OIZ2 is modulated by a sine-wave signal at the same frequency $f_1$ but with a phase angle $\theta$ (i.e. $Mod2=\sin(2\pi f_1 t+\theta)+1$). Total_Signal from a photodetector is the sum of the signal associated with emitted light from OIZ1 (Sig1) and OIZ2 (Sig2), respectively, and can be expressed as, $$\text{Total\_Signal}=\text{Sig1}+\text{Sig2}=S_1(t)(\sin(2\pi f_1 t)+1)+S_2(t)(\sin(2\pi f_1 t+\theta)+1) \quad (13)$$

where $S_1(t)$ and $S_2(t)$ are output electronic signal from the photodetector due to particles/cells passing through the $1^{st}$ OIZ and the $2^{nd}$ OIZ, respectively, when no modulation is applied to either one of the light sources. Note that for this example where the difference in modulation signals is based on phase angles, we will not consider the phase differences between the output electronic signal components and the modulation signals, as being described above in equations (1), (4), and (8). An electronic processor is used to demodulate the Total_Signal to recover electronic signal $S_1(t)$ and $S_2(t)$ so that the light intensity (i.e. fluorescence or side-scatter) can be derived at the corresponding detection channel. In one exemplary approach, two intermediate signals are derived by multiplying Total_Signal with a sine-wave signal with the same frequency as the modulation signal (i.e. $\sin(2\pi f_1 t)$) and a cosine-wave signal with the same frequency as the modulation signal (i.e. $\cos(2\pi f_1 t)$), respectively, then we have $$\begin{aligned}\text{Intermediate\_Signal\_1} &= \text{Toatl\_Signal} * \sin(2\pi f_1 t) \\ &= S_1(t)\sin(2\pi f_1 t)*\sin(2\pi f_1 t) + \\ &\quad S_1(t)\sin(2\pi f_1 t)+S_2(t)\sin(2\pi f_1 t)* \\ &\quad \sin(2\pi f_1 t)*\cos(\theta)+S_2(t)\sin(2\pi f_1 t)* \\ &\quad \cos(2\pi f_1 t)*\sin(\theta)+S_2(t)\sin(2\pi f_1 t) \\ &= 0.5S_1(t)-0.5S_1(t)\cos(4\pi f_1 t) + \\ &\quad S_1(t)\sin(2\pi f_1 t) + \\ &\quad 0.5S_2(t)\cos(\theta)-0.5S_2(t)\cos(\theta)\cos(4\pi f_1 t) + \\ &\quad 0.5S_2(t)\sin(\theta)\sin(4\pi f_1 t)+S_2(t)\sin(2\pi f_1 t)\end{aligned} \quad (14)$$

-continued $$\begin{aligned}
\text{Intermediate\_Signal\_2} &= \text{Total\_Signal} * \cos(2\pi f_1 t) \quad (15)\\
&= S_1(t)\sin(2\pi f_1 t)*\cos(2\pi f_1 t) +\\
&\quad S_1(t)\cos(2\pi f_1 t) + S_2(t)\cos(2\pi f_1 t)*\\
&\quad \sin(2\pi f_1 t)*\cos(\theta) + S_2(t)\cos(2\pi f_1 t)*\\
&\quad \cos(2\pi f_1 t)*\sin(\theta) + S_2(t)\cos(2\pi f_1 t)\\
&= 0.5 S_1(t)\sin(4\pi f_1 t) + S_1(t)\cos(2\pi f_1 t) +\\
&\quad 0.5 S_2(t)\cos(\theta)\sin(4\pi f_1 t) +\\
&\quad 0.5 S_2(t)\sin(\theta) + 0.5 S_2(t)\sin(\theta)\cos(4\pi f_1 t) +\\
&\quad S_2(t)\cos(2\pi f_1 t)
\end{aligned}$$

Similar to the analysis described above for equation (3) where the modulation frequency $f_1$ should be chosen properly to be more than two times of the signal bandwidth, low pass filters could be applied to filter Intermediate_Signal_1 and Intermediate_Signal_2, which results in $$\text{Filtered\_Intermediate\_Signal\_1} = 0.5 S_1(t) + 0.5 \cos(\theta) S_2(t) \quad (16)$$

and $$\text{Filtered\_Intermediate\_Signal\_2} = 0.5 \sin(\theta) S_2(t) \quad (17)$$

Thus, $S_1(t)$ and $S_2(t)$ could be recovered as $$S_2(t) = 2 \times \text{Filtered\_Intermediate\_Signal\_2}/\sin(\theta) \quad (18)$$

$$S_1(t) = 2 \times \text{Filtered\_Intermediate\_Signal\_1} - 2 \times \text{Filtered\_Intermediate\_Signal\_2} \times \cos(\theta)/\sin(\theta) \quad (19)$$

where phase angle θ should not be zero or 180 degree. Thus, equations (13), (18) and (19) illustrated the method for modulating two light sources based on phase-angles and the method for de-modulation to recover particle-induced electronic pulse signal $S_1(t)$ and $S_2(t)$. Modulation of different light sources based on different phase angles but the same modulation frequency (as described in an example shown in Eqn (13) through Eqn (19)) leads to simple electronics for generating such modulation signals, which becomes especially beneficial when the number of excitation light sources increases (e.g. ≥3 light sources). Preferably, for using the modulation signals having the same frequency but different phase angles as discussed in this example, the phase angle θ is preferably selected at 90 degree. Under such preferred embodiments, the low-pass filtered signal components in equations (16) and (17) become $$\text{Filtered\_Intermediate\_Signal\_1} = 0.5 S_1(t) \quad (20)$$

and $$\text{Filtered\_Intermediate\_Signal\_2} = 0.5 S_2(t) \quad (21)$$

Other methods of modulation and de-modulation could also be used for modulating light sources and recovering the modulated electronic pulse profiles generated as particles/cells pass through multiple optical interrogation zones. Those who are skilled in the art of electronics and electronic signal processing could readily employ various methods of modulation and de-modulation to achieve the required functionalities here. For example, as mentioned previously, modulation with square-wave forms or triangular-waveforms could also be applied to modulate light sources.

FIG. 3 illustrates one embodiment of the present invention where the flow cytometry comprises two excitation light sources (S1 and S2). FIG. 4 and FIG. 5 illustrate two examples of the method of the present invention for detecting the modulated light emitted from two different OIZs along a flow channel and for de-modulating and processing total detected electronic signals to recover and isolate the particle-induced electronic pulse profiles as particles/cells pass through each optical interrogation zone.

FIG. 6 and FIG. 7 illustrate additional examples of the method of the present invention for detecting the modulated light emitted from three different OIZs along a flow channel and for de-modulating and processing total detected electronic signals to recover and isolate the particle-induced electronic pulse profiles as particles/cells pass through each optical interrogation zone.

FIG. 6 shows the process of the analog modulation and de-modulation for an example of three light sources, two of which are intensity-modulated and one of which is not modulated. FIGS. 6A and 6B show the analog signals used to modulate the $1^{st}$ and $3^{rd}$ light source, respectively. In this example, modulation frequency for the $1^{st}$ and $3^{rd}$ light source is 3 MHz and 6 MHz, respectively. FIG. 6C shows the total detected electronic pulse signal if no modulation is employed for any of three light sources. A particle/cell passes through the $1^{st}$ OIZ, the $2^{nd}$ OIZ and the $3^{rd}$ OIZ sequentially and generate the $1^{st}$, $2^{nd}$ and $3^{rd}$ pulse, respectively. In this example, we assume that particle/cell diameter is 10 microns, passing through the OIZs with a 15 micron along the particle/cell flowing direction, and the linear velocity of the particle/cell is assumed to be 5 m/sec. Furthermore, we assume that the center-to-center distance between two adjacent OIZs is 30 microns. Therefore, the width of the generated individual particle-induced electronic pulse is estimated to be 5 μs (i.e. (10 μm+15 μm)/(5 m/s)) and the separation between two pulse peaks is estimated to be 6 μs (i.e. 30 μm/(5 m/s). FIG. 6D shows the total detected electronic signals when the $1^{st}$ and the $3^{rd}$ light sources are modulated using the modulation signals of FIG. 6A and FIG. 6B, respectively. Note that the $2^{nd}$ light source is not modulated. FIGS. 6E and 6F illustrates the intermediate signal when de-modulation is applied to the total signal of FIG. 6D to recover the $1^{st}$ pulse profile and $3^{rd}$ pulse profile, respectively. The intermediate signals shown in FIG. 6E and FIG. 6F are calculated by multiplying the detected electronic signals in FIG. 6D with the modulation sine-wave signal in FIG. 6A and FIG. 6B, respectively. FIGS. 6G, 6H and 6I show the recovered the $1^{st}$, the $2^{nd}$ and the $3^{rd}$ electronic pulse profiles, respectively, generated as the particle passes through the $1^{st}$, $2^{nd}$ and $3^{rd}$ light beams at three OIZs. The recovered electronic pulse signals are determined by low-pass filtering the intermediate de-modulation signals in FIG. 6E and FIG. 6F and by low-pass filtering the total detected electronic signals in FIG. 6C. Note that an amplification/scaling factor of 2 is applied to the signals on FIGS. 6G and 6I after the signals at FIGS. 6E and 6F are filtered by a low-pass filter with a cut-off frequency of 1 MHz.

FIG. 7 shows an additional example for the process of the analog modulation and de-modulation for a case of three light sources, two of which are intensity-modulated and one of which is not modulated. Different from the example in FIG. 6 where two light sources are modulated at different modulation frequencies. The two light sources being modulated in FIG. 7 are modulated at the same modulation frequency. FIG. 7A shows an analog sine-wave signal with a frequency of 3 MHz used to modulate the $1^{st}$ and $3^{rd}$ light source. FIG. 7B shows the total detected electronic pulse signal if no modulation is employed for any of three light sources. A particle/cell passes through the $1^{st}$ OIZ, the $2^{nd}$ OIZ and the $3^{rd}$ OIZ sequentially and generate the $1^{st}$, $2^{nd}$ and $3^{rd}$ pulse, respectively. In this example, we assume that particle/cell diameter is 10 microns, passing through the OIZs with a 15 micron along the particle/cell flowing direction, and the linear velocity of the particle/cell is assumed to be 5 m/sec. Furthermore, we assume that the center-to-center distance between two adjacent OIZs is 30 microns. Therefore, the width of the generated individual particle-induced electronic pulse is estimated to be 5 µs (i.e. (10 µm+15 µm)/(5 m/s)) and the separation between two pulse peaks is estimated to be 6 µs (i.e. 30 µm/(5 m/s). FIG. 7C shows the total detected electronic signals when the $1^{st}$ and the $3^{rd}$ light sources are modulated using the modulation signals of FIG. 7A. Note that the $2^{nd}$ light source is not modulated. FIG. 7D illustrates the intermediate signal when de-modulation is applied to the total signal of FIG. 7C to recover the $1^{st}$ and the $3^{rd}$ pulse profiles. The intermediate signal shown in FIG. 7D is calculated by multiplying the detected electronic signals in FIG. 7C with the modulation sine-wave signal in FIG. 7A. FIG. 7E shows the recovered $1^{st}$ and $3^{rd}$ electronic pulse profiles, generated by low-pass filtering the intermediate de-modulation signals in FIG. 7D. FIGS. 7F, 7G and 7H show the recovered $1^{st}$, $2^{nd}$ and $3^{rd}$ electronic pulse profiles, respectively, generated as the particle passes through the $1^{st}$, $2^{nd}$ and $3^{rd}$ light beams at three OIZs. Note that an amplification/scaling factor of 2 is applied to the signals on FIGS. 7E, 7F and 7H after the signals at FIG. 7D are filtered by a low-pass filter with a cut-off frequency of 1 MHz. In this example, the same modulation signal is used for modulating the $1^{st}$ and $3^{rd}$ light sources. Because the modulated light beams are focused/directed to different OIZs ($1^{st}$ OIZ and $3^{rd}$ OIZ) along the flow direction of the flow cell, it is possible to separate, isolate and identify the $1^{st}$ and $3^{rd}$ pulse profiles caused by particle traveling through the $1^{st}$ OIZ and the $3^{rd}$ OIZ, based on identifying appropriate time windows. Compared with the situation where the light sources are modulated with different modulation signals in FIG. 4 and FIG. 6, example shown in FIG. 7 where the same modulation signal and the same modulation frequency are used to modulate two different light sources, offers a special advantage such that a same signal processing circuit and software can be applied to de-modulate the electronic signals generated at the photodetectors associated with fluorescent molecules excited by two different light sources. This is beneficial to reducing over system complexity involved in signal processing. By using only one set of de-modulation and signal-recovery hardware and software for processing and de-modulating signals from two different light sources, more system resources could be available for processing various signals in the system, potentially improving signal to noise ratio for all fluorescence detections. In addition, since only one modulation frequency is used, choice of suitable modulation frequency would be more straightforward, compared with the case where two or more light sources are modulated at different modulation frequencies. This is especially true and important when the modulation signals have waveforms other than sine waves.

The flow cytometer system in the present invention can be coupled with a particle/cell sorting mechanism wherein particles or cells can be directed or sorted into different outlet chambers or containers after being detected at the optical interrogation zones. Such sorting would be based on the measurement and detection of fluorescent signals at different optical interrogation zones. Particles or cells of desired properties could be sorted together for further analysis or other usages. Various mechanisms of particle sorting, as being used in various commercial flow cytometers, can be applied to the particle sorting in the present invention. For example, in one approach, the flow of particles is controlled so that there is a large separation between particles relative to their diameter. A vibrating mechanism causes the stream of particles (or cells) to break into individual droplets. The particle concentration, the flow speed, droplet size and other parameters are adjusted so that there is a low probability of more than one cell per droplet. Immediately before the particle stream breaks into droplets, the particle flow passes through optical interrogation zones where the fluorescent properties or characteristics of each particle is determined and measured. An electrical charging mechanism is used to charge the droplet as it breaks from the stream, depending on whether particle being measured has the desired characteristics. The charged droplets then fall through an electrostatic deflection sub-system that diverts droplets into containers based upon their charge and thus upon their characteristics.

The system and method of the present invention for detecting emitted light excited by multiple light sources from multiple optical interrogation zones in a flow channel has a number of benefits.

Firstly, the approach does not require complex optical components/setup for collecting and separating light from multiple optical interrogation zones into optically/physically different positions in space for feasible detection. This would greatly simplify the optical collection optics setup and reduce the strict requirement for high accuracy of adjustment and alignment of the light collection lenses and positions of the subsequent filters and photodetectors. This is an advantage over the approach described in FIG. 1 where light from different OIZs need to be physically/optically separated.

Secondly, the approach uses simplified light-collection and detection setup (i.e. the emitted light with the same detection wavelength can be detected by the same set of filter and photodetector even though they are excited by different light sources). This is an advantage over the approach described in FIG. 1 where different optical filter and photodetector is needed for detecting emitted light from different light sources even though the detection wavelength range is the same. Simplified light-collection optics and detection setup reduces the complexity of the system and thus the cost.

Thirdly, light emitted from different OIZs due to different excitation light sources can be detected and determined by exploiting modulation and de-modulation in electronics field, allowing the system to work with different fluorescent molecules with same/overlapped emission spectra in the same experiment. This is an advantage over the approach described in FIG. 2 where the system could not distinguish different fluorescent molecules having same/overlapped emission spectra but excited by different excitation light sources.

Fourthly, the modulation of the excitation light sources and de-modulation of the detected electronic signals is independent between different light sources. This is an advantage over the approach described in U.S. Pat. No. 7,990,525 where accurate control of the time-multiplexed illumination of multiple excitation light beams is essential and so as the subsequent synchronization of the signal processing electronics.

Furthermore, the system and method of the present invention for detecting emitted light excited by multiple light sources from multiple optical interrogation zones in a flow channel surprisingly achieves a number of additional benefits.

Firstly, directing light beams from multiple excitation sources into different OIZs at different locations along the flow channel in the present invention provides a further benefit that the full dynamic range of the photodetector and associated electronics circuits could be efficiently exploited/utilized for each analyzed fluorescent molecules. This is an advantage over the approach described in FIG. 2 where multiple excitation light beams are directed to the same location in the flow channel. In FIG. 2, unless at any given time moment, only one light source is activated (i.e. turned on), light emitted from different types of fluorescent molecules having the same/overlapped emission spectra but excited by different light sources would be mixed together and the corresponding electronic pulses would be superimposed on each other. This leads to actual reduction of the upper limit of the detecting range for each of analyzed fluorescent molecules. For example, in FIG. 2, assume that two types of fluorescent molecules are used and they can only be excited by two different light sources but emit fluorescent light with overlapped spectra. If the condition (e.g., the number of fluorescent molecules per particle/cell, the energy of light beams from two excitation light sources, the fluorescence-generating efficiency of the fluorescent molecules, etc.) for these two types of fluorescent molecules is similar, then the total detected signal from the same photodetector would be the signal from both fluorescent molecules added together. Since the dynamic range of the photodetector is a fixed value, the upper limit of the detecting range for each fluorescent signal would be reduced by half assuming full dynamic range of the photodetector is used. For the present invention, fluorescent molecules with overlapped emission spectra will be excited at different OIZs at different locations along the flow channel. Thus, by properly choosing the center-to-center distance of adjacent light beams at different OIZs, probability of two particles/cells being both within two OIZs is minimized or very low. Therefore, at any given time moment, the photo-detector only detects the emission light from one type of fluorescent molecule, allowing for the efficient use of the full dynamic range of the photodetector.

Secondly, directing light beams from multiple excitation light sources into different OIZs at different locations along the flow channel in the present invention has a further benefit of improved sensitivity in detecting low-light-emitting, dimly-stained fluorescent particles/cells. This is an advantage over the approach described in FIG. 2 where multiple excitation light beams are directed to a single OIZ in the flow channel. In FIG. 2, unless at any given time moment, only one light source is activated (i.e. turned on), light emitted from different types of fluorescent molecules having the same/overlapped emission spectra but excited by different light sources would be mixed together and the corresponding electronic pulses would be superimposed on each other. Light emitted from one type of fluorescent molecule would become the background for light emitted from the other type(s) of fluorescent molecules, and vice versa. Such "mutual background" of light emitted from different types of fluorescent molecules would reduce the sensitivity for detecting dimly stained fluorescent particles/cells because it might be embedded in a strong fluorescent signal from another fluorescent molecule excited by another light source. For the present invention, light emitted from each type of fluorescent molecule is only excited at a single OIZ at a single location of the flow channel. Thus, by properly choosing the center-to-center distance of adjacent light beams at different OIZs, probability of two particles/cells being both within two OIZs is minimized or very low. The only background light comes from the stray light of the flow channel and the optical set up. Thus, detection of low or dim fluorescent signals could be possible using present invention.

Thirdly, the approach of different modulations applied to different light sources and the approach of recovering emitted light components due to different light sources based on their modulation methods in the present invention has a further benefit that there is no very accurate/precise requirement for separation distance between different OIZs. The de-modulation and electronic signal recovery means can effectively recover the light-intensity-dependent electronic signal pulse due to each light source by effective modulation method for the corresponding light source and as long as the light beams directed at different OIZs are kept relatively stable over the time scale required for a particle/cell passing through an OIZ. The small variation in separation distance between different OIZs does not affect the measurement results since the particle-induced electronic pulse signals could be recovered through de-modulation and the positioning of such pulses could be readily identified through an analysis algorithm. This simplifies the requirement for the optical sub-system for delivering/directing light beams into different OIZs. This is an advantage over the approaches shown in FIG. 1 and FIG. 2. In FIG. 1, it is essential to keep and maintain the different light beams at different OIZs at an accurately controlled distance, since the variation in this distance would affect the efficiency of the light collection from each OIZ, leading to unreliable measurement results of the fluorescent signals. In FIG. 2, the different light beams from different excitation light sources are required to be aligned coaxially to the same OIZ at a single location in the flow channel. A complex optical setup is required to achieve such accurate control of the relative positions of the light beams. Any disturbance of the optical system, such as temperature, pressure, misalignment during instrument shipping, or other system instability factors would cause the beams not coaxially aligned and might leads to misinterpretation of collected signals. On the other hand, for the present application, there is no very accurate/precise requirement for separation distance between different light beams (i.e. the separation distance between adjacent OIZs). Thus, the optical sub-system for delivering light beams to the flow channel could be simplified and easy to maintain.

Fourthly, the present invention has a further benefit of achieving higher signal-to-noise ratio due to the modulation/de-modulation method it employed. As described above in several examples shown in Eqn (1) through Eqn (11), the de-modulation for recovering the particle-induced electronic pulse profile involves a low-pass filtering procedure based on the bandwidth of the particle-induced electronic pulse. Such low-pass filtering can effectively remove the high-frequency noises signals in the system, such as the thermal noises of the electronic elements. Therefore, the overall signal-to-noise ratio could be improved using present invention.

What is claimed is:

1. A system for detecting signal components of light induced by multiple excitation sources, comprising:
   a flow channel configured for the flow of particles, the flow channel comprising three spatially separated optical interrogation zones;
   a first excitation source configured to direct a light beam of a first wavelength at a near constant intensity onto a first of the optical interrogation zones, wherein the light beam of the first wavelength is not intensity modulated;
   second and third excitation sources, wherein the second excitation source is configured to direct a light beam of a second wavelength onto a second of the optical interrogation zones, and the third excitation source is configured to direct a light beam of a third wavelength onto a third of the optical interrogation zones, wherein the second wavelength is different from the first wavelength and the light beams of the second and third wavelength are intensity modulated at a same frequency;

a detector subsystem comprising a set of detectors configured to detect light emitted from particles flowing through the optical interrogation zones and to convert the detected light into a total electrical signal comprising modulated and unmodulated electrical signals; and a processor configured to receive the total electrical signal from the detector subsystem, to de-modulate the modulated electrical signal, and to determine signal components from the light detected from each of the optical interrogation zones.

2. The system according to claim 1, wherein the optical interrogation zones are spaced from about 30 to about 80 microns apart.

3. The system according to claim 1, wherein each excitation source is a laser or a light emitting diode (LED).

4. The system according to claim 1, wherein the first wavelength and the second wavelength are each different wavelengths, each of which is selected from the group consisting of about 325, nm, 355 nm, 365 nm, 375 nm, 405 nm, 407 nm, 488 nm, 532 nm, 561 nm, 595 nm, 633 nm, 635 nm, 640 nm, and 647 nm.

5. The system according to claim 1, wherein the modulating frequency is between 1 MHz and 100 MHz.

6. The system according to claim 1, wherein the modulating excitation sources are modulated according to a waveform selected from the group consisting of a sine waveform, a square waveform, a triangular waveform and a seesaw waveform.

7. The system according to claim 1, wherein the set of detectors selectively detect wavelengths of about 421±30 nm, 450±30 nm, 455±40 nm, 519±30 nm, 530±15 nm, 578±15 nm, 585±40 nm, 603±30 nm, 615±30 nm, 620±30 nm, >650 nm, 660±10 nm, 667±30 nm, 668±30 nm, 678±30 nm, 695±25 nm, >750 nm, 780±30 nm and >785 nm.

8. The system according to claim 1, wherein the system further comprises light collecting and light splitting optics between the flow channel and detector subsystem.

9. The system according to claim 8, wherein the light collecting and light splitting optics are shared to collect light emitted from each of the optical interrogation zones and to split light into multiple light detection channels.

10. The system according to claim 1, further comprising a sorting mechanism configured to sort a flowing particle population into one or more chambers in response to commands from the processor.

11. A method of detecting signal components from light induced by multiple excitation sources, the method comprising:

providing a flow channel comprising three spatially separated optical interrogation zones;

flowing a population of particles labeled with at least two different fluorescent molecules through each of the optical interrogation zones;

directing a light beam of a first wavelength at a near constant intensity at a first of the optical interrogation zones to induce emission of light from the fluorescence-molecule containing particles;

directing a light beam of a second wavelength with an intensity modulated over time according to a modulating frequency onto a second of the optical interrogation zones to induce emission of light from the fluorescence-molecule containing particles, wherein the second wavelength is different from the first wavelength;

directing a light beam of a third wavelength with an intensity modulated over time according to a same modulating frequency as the light beam of the second wavelength onto a third of the optical interrogation zones;

detecting the light emitted from the particles from each of the optical interrogation zones and converting detected light into a total electrical signal, which comprises modulated and unmodulated electrical signal;

de-modulating the modulated electrical signal from the total electrical signal; and determining signal components of the light detected from each of the optical interrogation zones.

12. The method according to claim 11, wherein the fluorescent molecules emits fluorescence at a wavelength selected from the group consisting of 519 nm, 578 nm, 640 nm, 660 nm, 785 nm.

13. The method according to claim 11, wherein the third wavelength is different from the first and second wavelengths.

14. The method according to claim 11, further comprising sorting the cell population into one or more chambers according to the presence or absence of one or more detected components.

* * * * *